United States Patent [19]

Venkatesan et al.

[11] Patent Number: 5,290,780
[45] Date of Patent: Mar. 1, 1994

[54] ANGIOTENSIN II RECEPTOR BLOCKING 2,3,6 SUBSTITUTED QUINAZOLINONES

[75] Inventors: Aranapakam Venkatesan, Elmhurst; Jeremy I. Levin, Spring Valley, both of N.Y.

[73] Assignee: American Cyanamid Co., N.J.

[21] Appl. No.: 818,721

[22] Filed: Jan. 14, 1992

Related U.S. Application Data

[63] Continuation-in-part of Ser. No. 648,492, Jan. 30, 1991, abandoned.

[51] Int. Cl.$^5$ .............. A61K 31/505; C07D 403/10; C07D 239/91
[52] U.S. Cl. .................. 514/259; 544/284; 544/287
[58] Field of Search .......... 544/287, 284, 287; 514/259

[56] References Cited

U.S. PATENT DOCUMENTS

| | | | |
|---|---|---|---|
| 4,797,403 | 1/1989 | Lowe, III | 514/259 |
| 4,992,550 | 2/1991 | Hughes | 544/284 |
| 5,240,928 | 9/1993 | Allen et al. | 514/259 |

FOREIGN PATENT DOCUMENTS 0367944  5/1990  European Pat. Off. .

OTHER PUBLICATIONS

Chiu et al., European Journal of Pharmacology 157(1988) 13-21.

*Primary Examiner*—Mukund J. Shah
*Assistant Examiner*—Matthew V. Grumbling
*Attorney, Agent, or Firm*—Thomas S. Szatkowski

[57] ABSTRACT

Novel quinazolinone compounds of the formula:

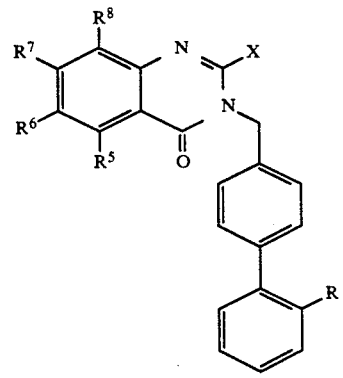

wherein $R^5$, $R^6$, $R^7$, $R^8$, R and X are defined in the specification, which have angiotensin II (AII) antagonizing activity, intermediates useful in the preparation of the compounds, methods of producing and using the compounds to alleviate angiotensin induced hypertension and treat congestive heart failure in mammals.

5 Claims, 7 Drawing Sheets

ANGIOTENSIN II RECEPTOR BLOCKING 2,3,6 SUBSTITUTED QUINAZOLINONES

This is a continuation-in-part of copending application Ser. No. 07/648,492 filed on Jan. 30, 1991 now abandoned.

BACKGROUND OF THE INVENTION

1. Field of the Invention

This invention relates to certain novel 2, 3, 6 substituted quinazolinone compounds which have demonstrated enhanced in vivo activity as angiotensin II (AII) antagonists and are therefore useful in alleviating angiotensin induced hypertension and for treating congestive heart failure.

2. Description of the Prior Art

The enzyme renin acts on a blood plasma $\alpha_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

Furukawa et al., in U.S. Pat. No. 4,340,598, issued Jul. 20, 1982, discloses hypotensive and angiotensin II receptor blocking imidazole derivatives of the formula:

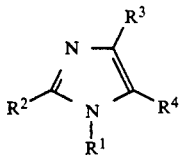

wherein $R^1$ is lower alkyl or phenyl $C_{1-2}$ alkyl optionally substituted with halogen or nitro; $R^2$ is lower alkyl, cycloalkyl or phenyl optionally substituted; one of $R^3$ and $R^4$ is $-(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, n=1 and $R^5$ is lower alkoxyl or hydroxyl; and salts thereof.

Furukawa et al., in European Patent Application No. 103,647 discloses 4-chloro-2-phenylimidazole-5-acetic acid derivatives useful for treating edema and hypertension and have angiotensin II receptor blocking activity of the formula:

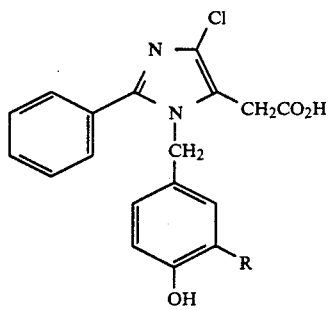

where R represents lower alkyl and salts thereof.

D. J. Carini, et al. in published European Patent Applications No. 87109919.8, filed Sep. 7, 1987 and No. 89100144.8, filed May 1, 1989 disclose angiotensin II receptor blocking imidazoles of the formula:

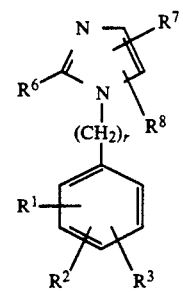

wherein the definitions of the substituents may be found within the applications.

P. Aldrich et al., in U.S. Pat. No. 4,874,867, issued Oct. 17, 1989, describes tetrazole intermediates of the formula:

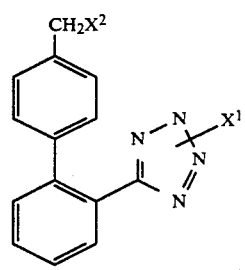

wherein $X^2$ and $X^1$ are defined therein. These intermediates are described as useful for producing compounds which are useful as inhibitors of the hormone angiotensin II (AII).

D. J. Carini et al., in U.S. Pat. No. 4,880,804, issued Nov. 14, 1989, described substituted benzimidazoles useful as inhibitors of the hormone angiotensin II (AII) of the formula:

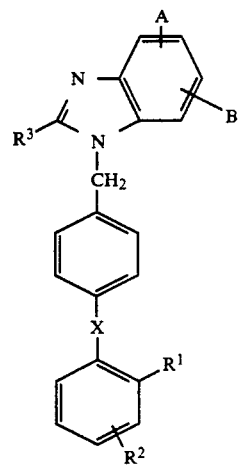

wherein $R^1$ is $-CO_2H$, $-NHSO_2CF_3$, or

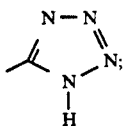

$R^2$ is H, halogen, $NO_2$, methoxy, or alkyl of 1 to 4 carbon atoms; $R^3$ is alkyl of 1 to 6 carbon atoms, alkenyl or alkynyl of 3 to 6 carbon atoms both of which may be optionally substituted with a halogen atom, $-OR^4$ or up to two $-CO_2R^4$; with the proviso that when $R^3$ is methyl, it must be substituted with $-OR^4$ or $-CO_2R^4$; $R^4$ is H, or alkyl of 1–4 carbon atoms; A is H, alkyl of 1 to 10 carbon atoms, $C_rF_{2r+1}$ where $r=1$–6, $C_6F_5$, halogen, alkoxy of 1 to 6 carbon atoms;

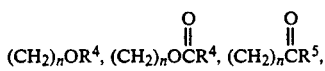

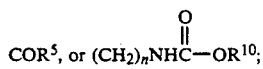

B is H, alkyl of 1 to 10 carbon atoms, $C_rF_{2r+1}$ where $r=1$–6, $C_6F_5$, halogen or alkoxy of 1 to 6 carbon atoms; X is a carbon-carbon single bond, $-CO-$, $-O-$, $-NHCO-$, or $-OCH_2-$.

D. J. Carini et al. in published European Patent Application No. 89100142.2, filed May 1, 1989, discloses angiotensin II receptor blocking pyrroles, pyrazoles and triazoles such as:

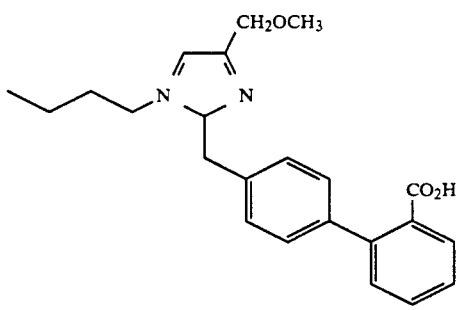

and

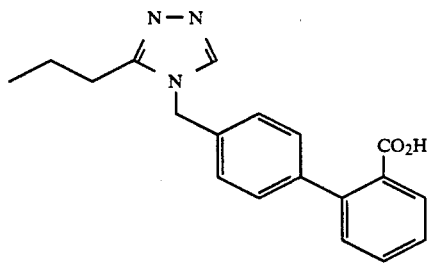

There has been no teaching or suggestion that the heretofore known antagonists of AII have the quinazolinone structure.

SUMMARY OF THE INVENTION

According to the present invention, there are provided novel compounds of Formula I which have enhanced in vivo angiotensin II-antagonizing properties and are useful as antihypertensives:

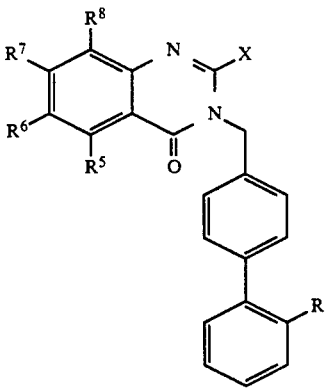

Formula I wherein:
R is

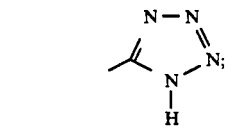

X is straight or branched alkyl of 3 to 5 carbon atoms; n is 1 to 3; $R^5$ is H; $R^6$ is

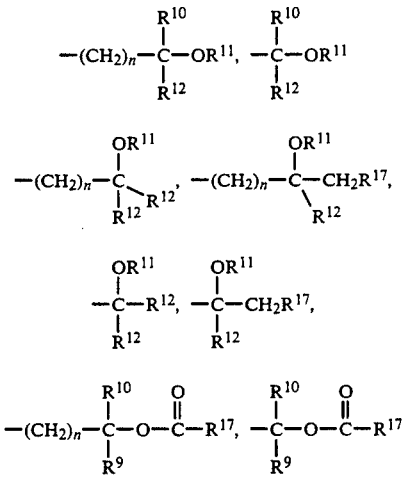

where
$R^9$ is H, straight chain lower alkyl of 1 to 4 carbon atoms, phenyl, substituted phenyl (substitution selection from mono-lower alkyl of 1 to 3 carbon atoms, $-CF_3$, nitro, O-alkyl of 1 to 3 carbon atoms, $NH_2$), pyridine, thiophene, or furan;

$R^{10}$ is H, straight chain lower alkyl of 1 to 4 carbon atoms, phenyl, substituted phenyl (substitution selection from mono-lower alkyl of 1 to 3 carbon atoms, $-CF_3$, nitro, O-alkyl of 1 to 3 carbon atoms, $NH_2$), pyridine, thiophene, or furan;

provided, however, that $R^9$ and $R^{10}$ cannot both be H, $R^{11}$ is H, straight chain or branched lower alkyl of 1 to 4 carbon atoms;

$R^{12}$ is straight chain lower alkyl of 1 to 4 carbon atoms, phenyl, substituted phenyl (substitution selection from mono-lower alkyl of 1 to 3 carbon atoms, —CF₃, nitro, O-alkyl of 1 to 3 carbon atoms, NH₂), pyridine, thiophene, or furan;

R¹⁷ is straight or branched lower alkyl of 1 to 4 carbon atoms;

R⁷ and R⁸ are H; and pharmaceutically acceptable salts of these compounds.

The present invention also provides novel intermediate compounds, methods for making the novel 2, 3, 6 substituted quinazolinone angiotensin II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

Figure 1:
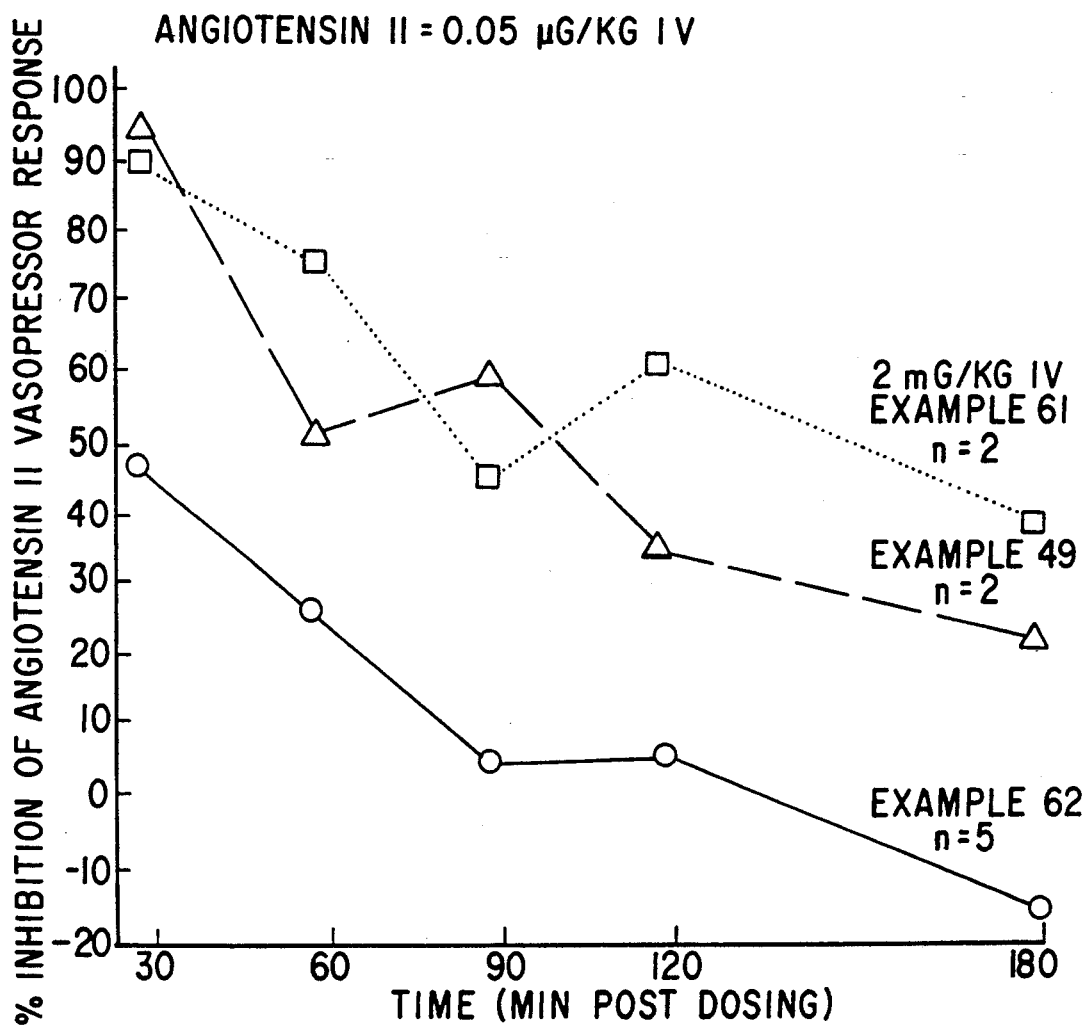
FIG. 1 depicts data showing antagonism of the vasopressor response of Antiotensin II in spontaneously hypertensive rats.
Figure 2:
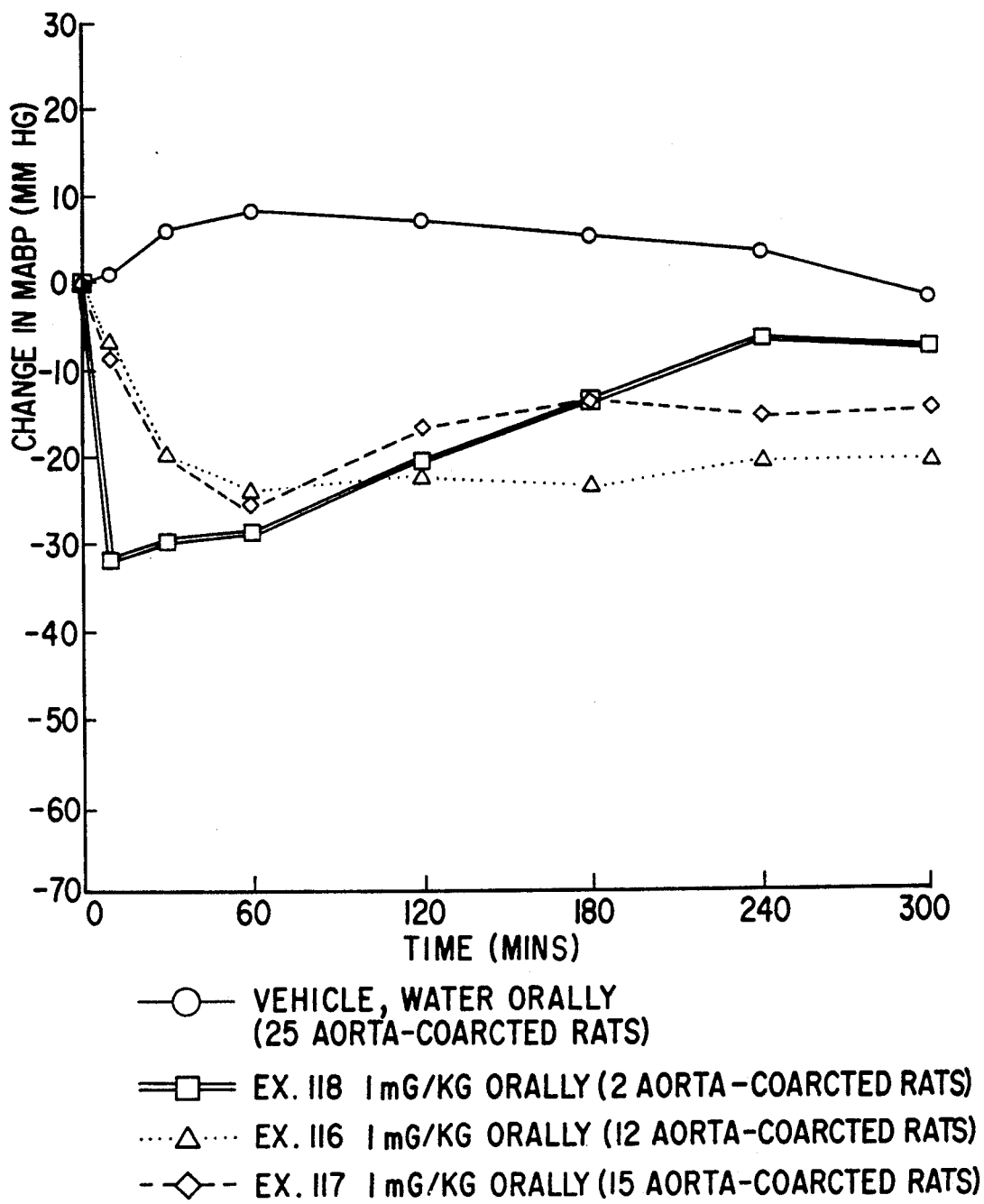
FIGS. 2-7 depict mean average blood pressure response data in aorta-coarcted hypertensive rats.
Figure 3:
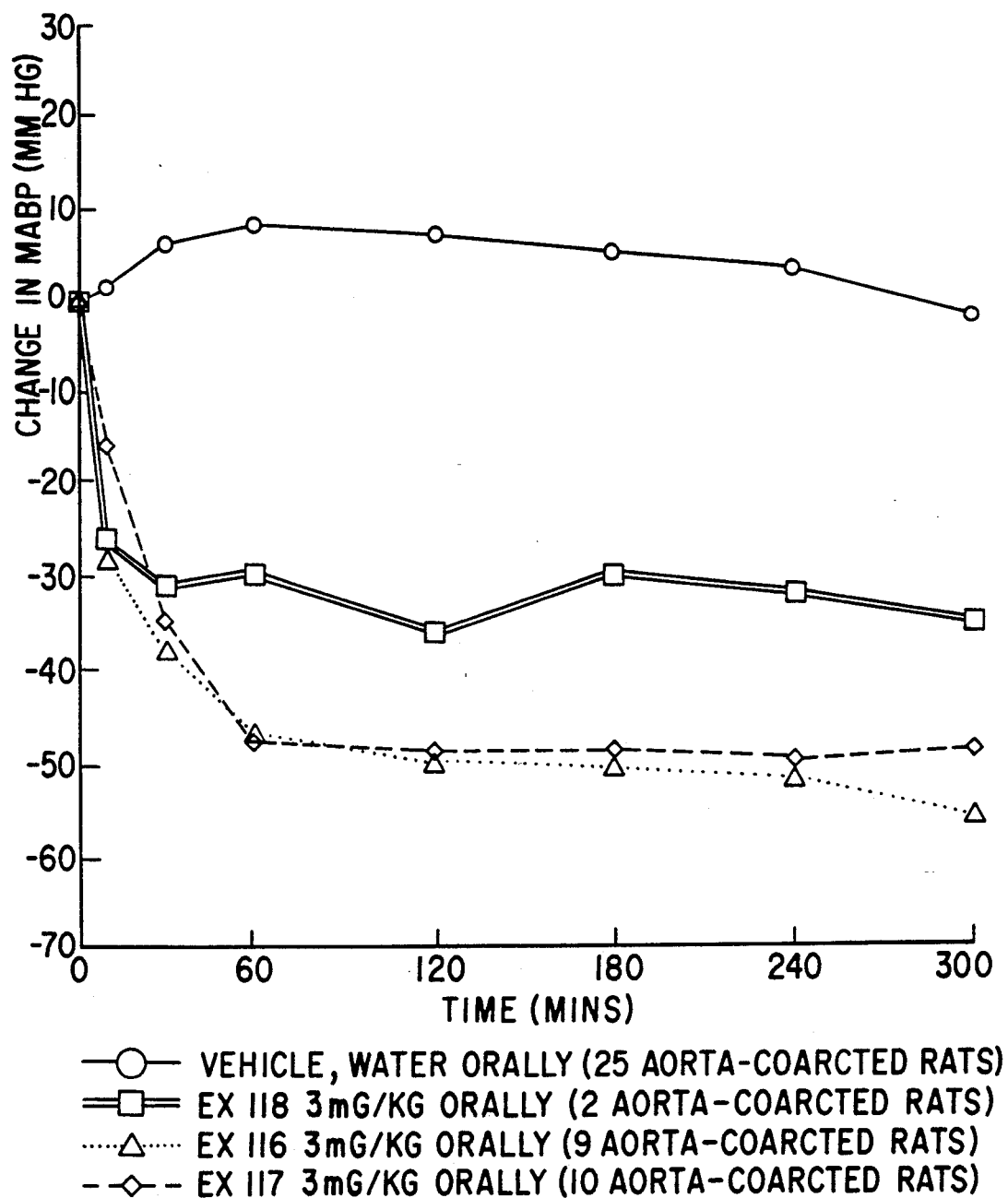
Figure 4:
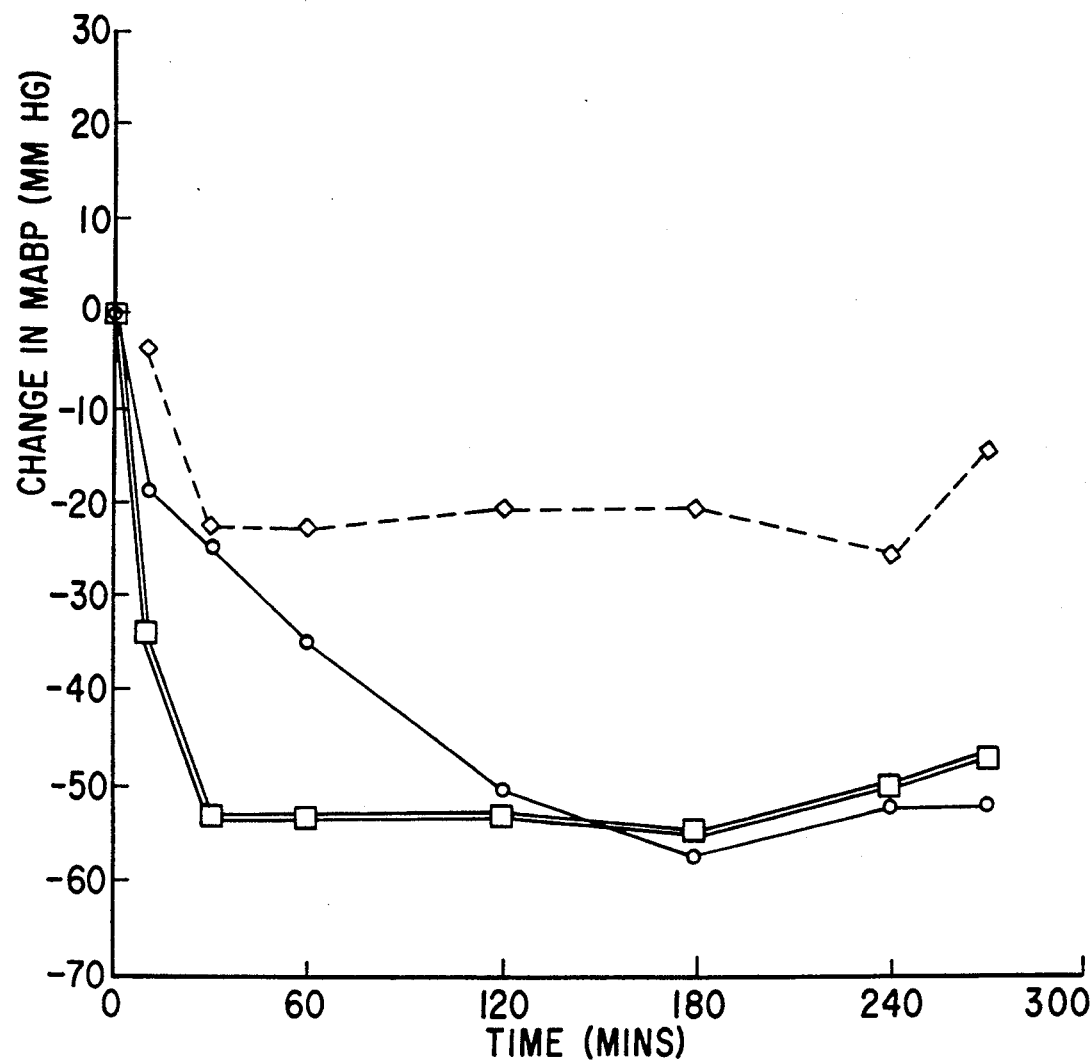
Figure 5:
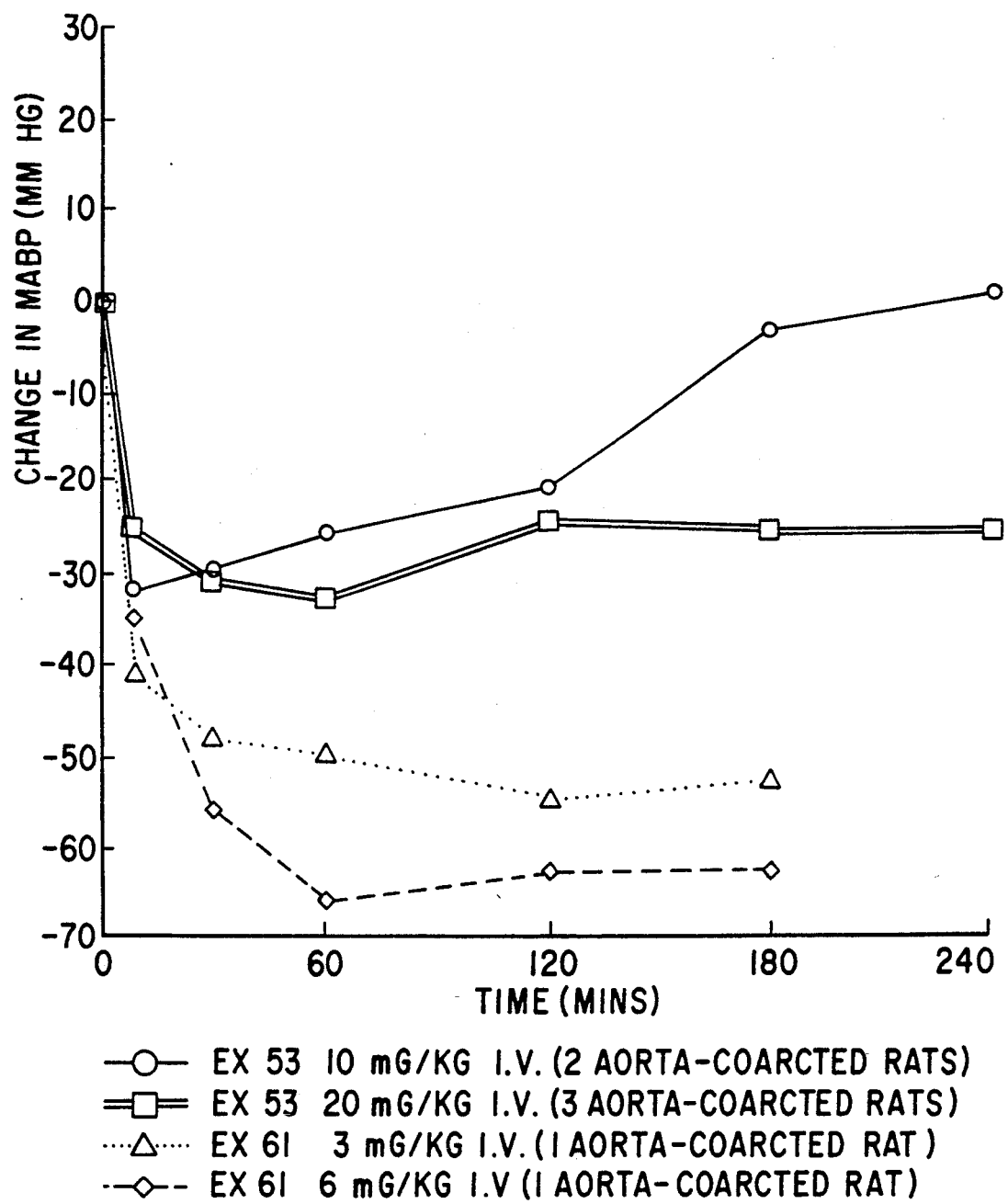
Figure 6:
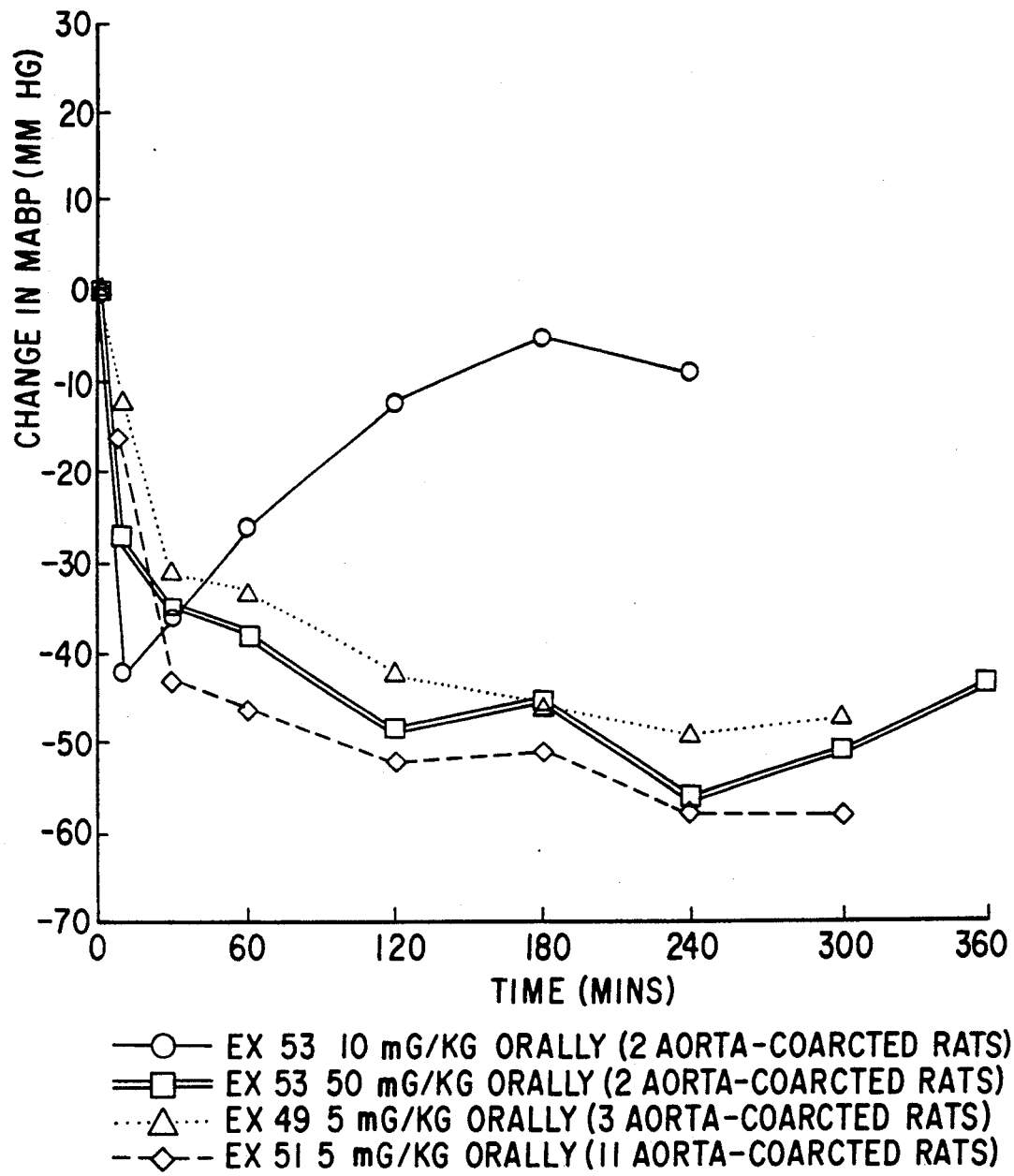
Figure 7:
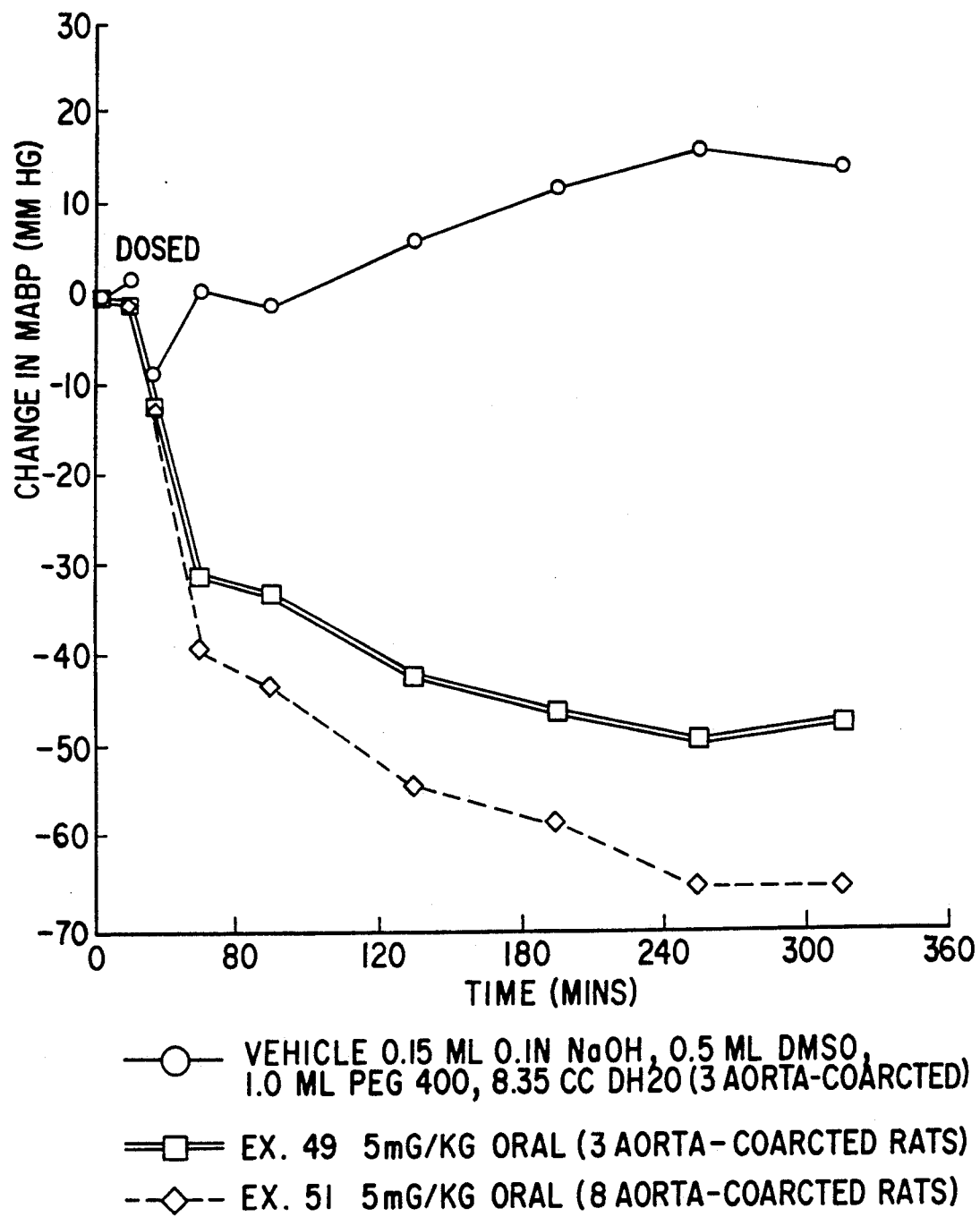

The novel compounds of the present invention are prepared according to the following reaction schemes.

Referring to Method A, the quinazolinone intermediates of Formula 5, are prepared from the corresponding substituted anthranilic acids 2 wherein the substituents R⁵, R⁶, R⁷ and R⁸ are described hereinabove except R⁶ may not be:

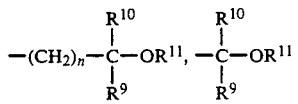

The corresponding anthranilic acid 2 is heated to reflux in alkyl acid anhydride 3 wherein X is alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained. To prepare compounds for which R⁶, has been excluded from this method, refer to Schemes I to X herein.

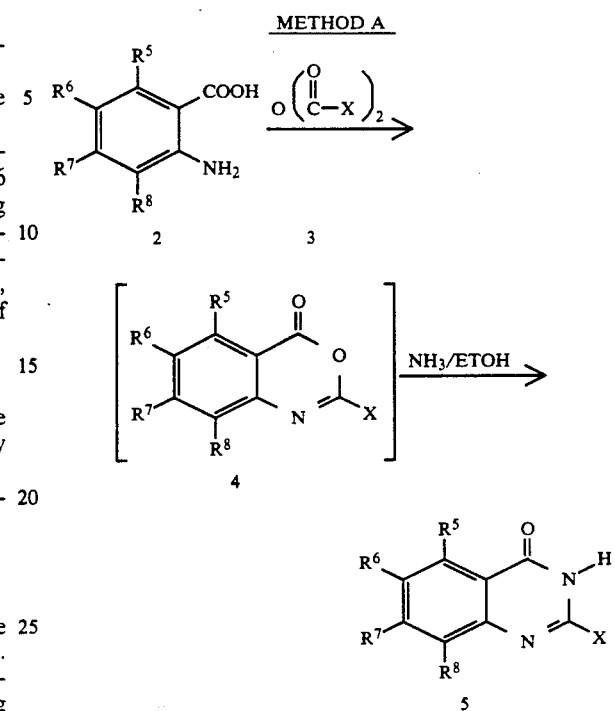

Referring to Method B, the method of B. Baker, et al., *J. Org. Chem.* 17, 157 (1952) is used to convert the appropriate substituted aniline 6 into quinazolinone 5 wherein the substituents R⁵, R⁶, R⁷ and R⁸ are described hereinabove except they may not be as follows:

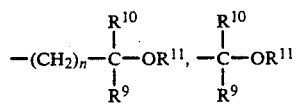

The substituted aniline 6 is reacted with chloral and hydroxylamine hydrochloride to afford an oxime 7 which is cyclized to the isatin 8 in the presence of sulfuric acid. The isatin 8 is then hydrolyzed to the anthranilic acid 9 using 30% aqueous hydrogen peroxide and aqueous sodium hydroxide. Further reaction as in Method A yields the quinazolinone intermediate 5. To prepare compounds for which R⁶, has been excluded from this method, refer to Schemes I to X herein.

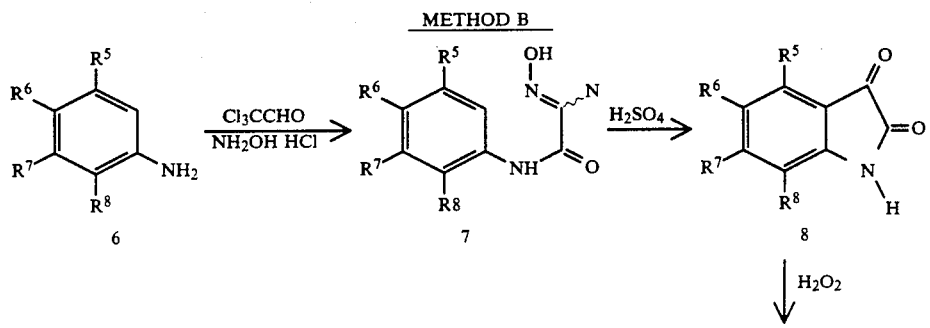

METHOD B

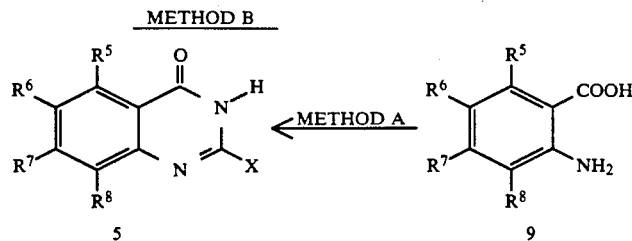

A general reference to the synthesis of 3,4-dihydro-4-oxo-quinazolines 5 is given in "The Chemistry of Heterocyclic Compounds, Fused Pyrimidines. Part I: Quinazolines", W. L. F. Armarego; Interscience Publishers (1967), pp. 74-94. Additional references are described in "Heterocyclic Compounds", Vol. 6, p. 334, R. C. Elderfield (Editor), Wiley and Sons, 1957.

Quinazolinone intermediates 5 are then modified according to the following schemes to obtain the novel 2, 3, 6 substituted quinazolinone Angiotensin II antagonizing compounds of the present invention.

In Scheme I, 6-methylquinazolinone 10, as prepared by method A, is brominated with N-bromosuccinimide to give the bromomethyl compound 11. Hydrolysis of the bromide with aqueous potassium carbonate in dimethylsulfoxide yields the primary alcohol 12.

The alcohol 12 is oxidized with pyridinium dichromate in N,N-dimethylformamide to afford aldehyde 13. The aldehyde 13 is reacted with a variety of Grignard Reagents $R^{12}MgBr$ or lithium reagents $R^{12}Li$ in tetrahydrofuran wherein $R^{12}$ is selected from straight or branched alkyl of 1 to 4 carbon atoms, phenyl, substituted phenyl, pyridyl, thiophene and furan, to give the desired secondary alcohol 14.

SCHEME 1

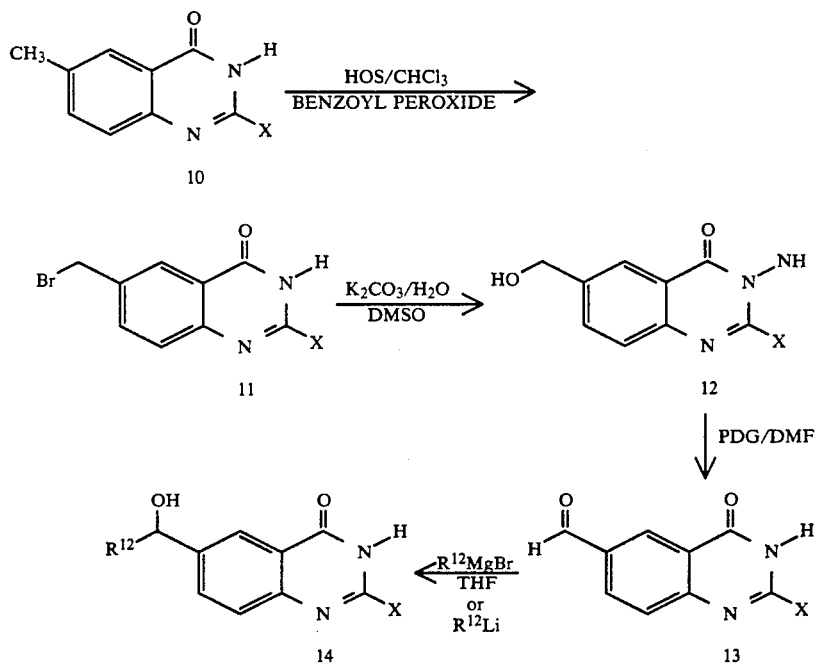

In an alternate route to 13, as shown in Scheme II, 2-alkylsubstituted-6-iodo-4(1H)-quinazolinone 15, prepared by method A is reacted via a palladium catalyzed carbonylation to give aldehyde 13.

Ester 16 is formed by palladium (II) catalyzed coupling of 2-alkylsubstituted-6-iodo-4(1H)-quinazolinone 15 with carbon monoxide and methanol. Further derivatization of 16 with an excess of Grignard $R^{12}MgX$ or $R^{12}Li$ affords tertiary alcohol 17 where $R^{12}$ is hereinbefore defined.

SCHEME II

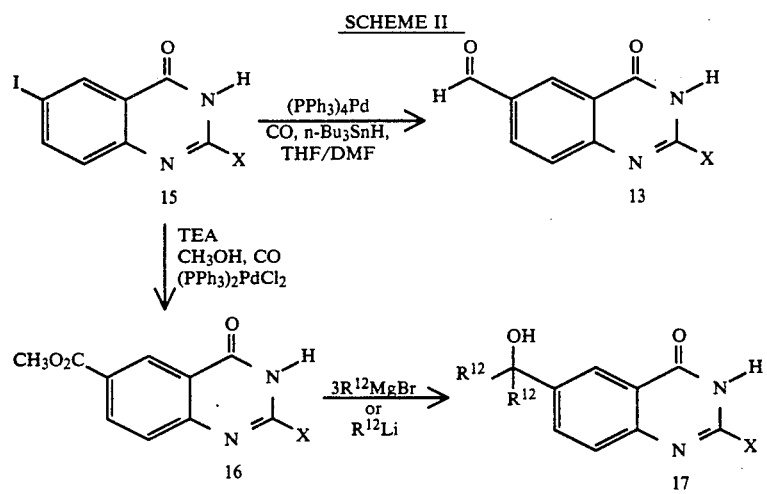

The synthetic pathway to tertiary alcohol substituted quinazolinones is shown in Scheme III.

lenic quinazolinone 21. Desilylation of the acetylene with sodium hydroxide in water-methanol gives the

Scheme III

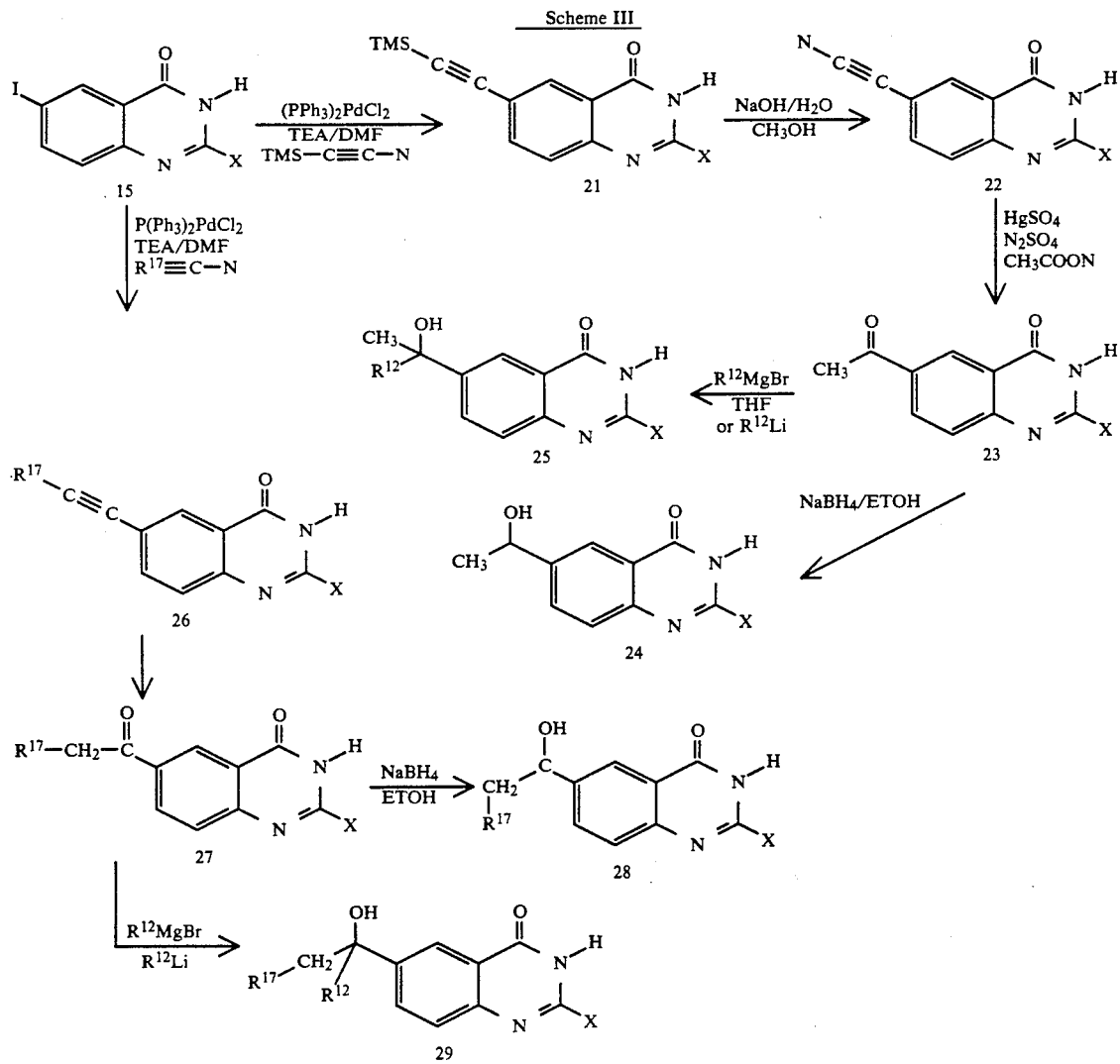

As shown in Scheme III, the palladium (II) catalyzed coupling of (trimethylsilyl)acetylene with 2-alkylsubstituted-6-iodo-4(1H)-quinazolinone 15 yields the acetyterminal acetylene 22. Hydration with catalytic mercuric sulfate-sulfuric acid in acetic acid affords methyl ketone 23. Reduction of ketone 23 with sodium borohydride in ethanol gives secondary alcohol 24. Alternatively, methyl ketone 23 is reacted with Grignard reagents $R^{12}MgBr$ or lithium reagent $R^{12}Li$ where $R^{12}$ is as defined before to yield tertiary alcohols 25. The palladium (II) catalyzed coupling of substituted acetylenes where $R^{17}$ is defined as straight or branched lower alkyl of 1 to 4 carbon atoms with 2-alkylsubstituted-6-iodo-4(1H)-quinazolinone 15 yields the acetylenic quinazolinone 26. Hydration of 26 with catalytic mercuric sulfate-sulfuric acid in acetic acid gives ketone 27. Reduction of ketone 27 with sodium borohydride in ethanol gives secondary alcohol 28. Reaction of ketone 27 with Grignard reagent $R^{12}MgBr$ or lithium reagent $R^{12}Li$ where $R^{12}$ is as defined before yields alcohol 29.

Carboxylic acid 77, prepared by Method A, as presented in Scheme IV, is converted to the ethyl ester 78 by reaction with ethyl alcohol containing a catalytic amount of sulfuric acid. Reduction of 78 with lithium aluminum hydride in tetrahydrofuran affords alcohol 79. Alcohol 79 is oxidized with pyridinium dichromate to yield aldehyde 80.

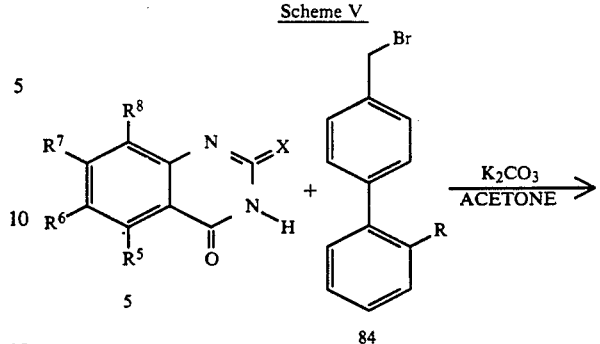

Scheme V

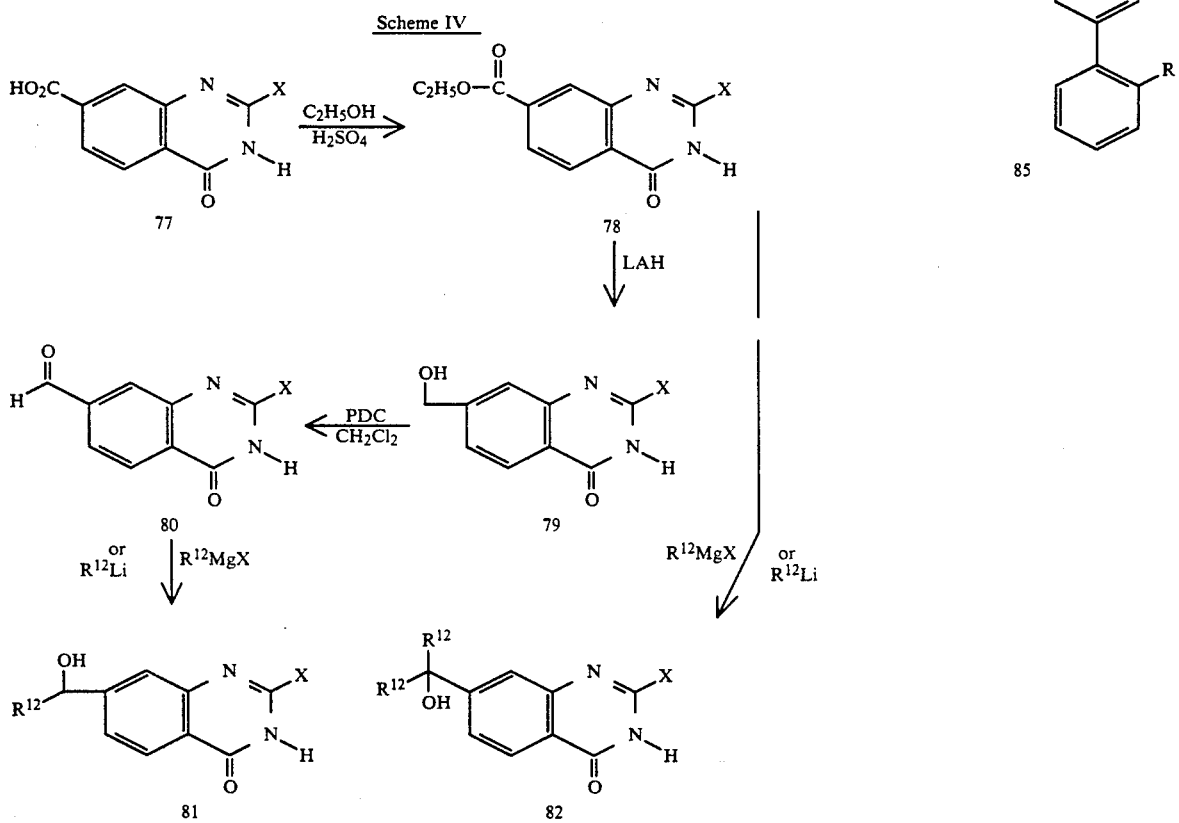

Scheme IV

Reaction of aldehyde 80 with Grignard reagent $R^{12}MgBr$ or lithium reagent $R^{12}Li$, where $R^{12}$ is hereinbefore defined, affords alcohol 81. Also, ethyl ester 78 is reacted with Grignard reagent $R^{12}MgBr$ or lithium reagent $R^{12}Li$ to give alcohol 82.

The coupling of a quinazolinone intermediate 5 to a biphenyl tetrazole 84 where R is as defined before, which are prepared by the methods of P. E. Aldrich et al., U.S. Pat. No. 4,874,867, issued Oct. 17, 1989, is illustrated in Scheme V.

The quinazolinone 5 and the biphenyl 84 are dissolved in acetone or another suitable solvent such as N,N-dimethylformamide, N,N-dimethylacetamide, N- methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, sodium t-butoxide or potassium t-butoxide for 2-24 hours, at 20°-60°. The obtained alkylated quinazolinones 85 may be purified by chromatography or used as is in further transformations and/or deprotection.

In those cases where the R in the alkylated quinazolinones 85 is a trityl tetrazole, deprotection of the trityl group, as outlined in Scheme VI, is accomplished by refluxing an aqueous acetone solution of the alkylated quinazolinone 86 with a catalytic amount of hydrochloric acid or other suitable acid such as sulfuric, trifluoroacetic or hydrogen chloride for 2-24 hours. The resulting tetrazoles 87 are isolated by flash chromatography or by trituration with ether and collection by filtration.

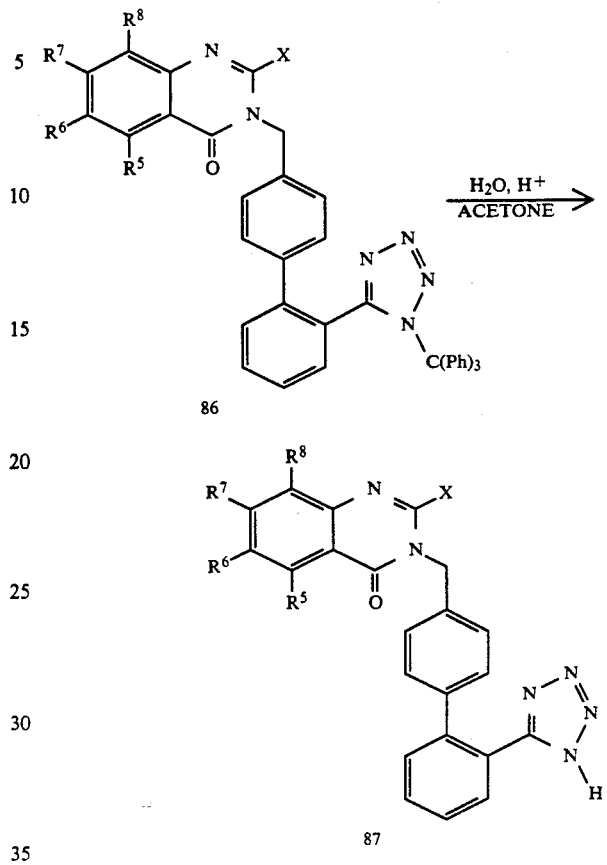

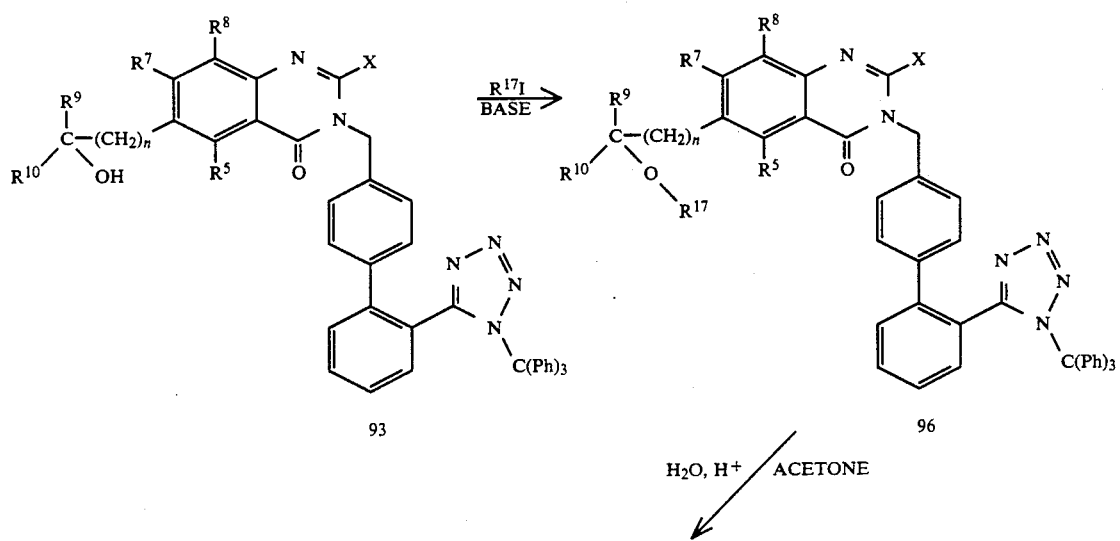

-continued
Scheme VII

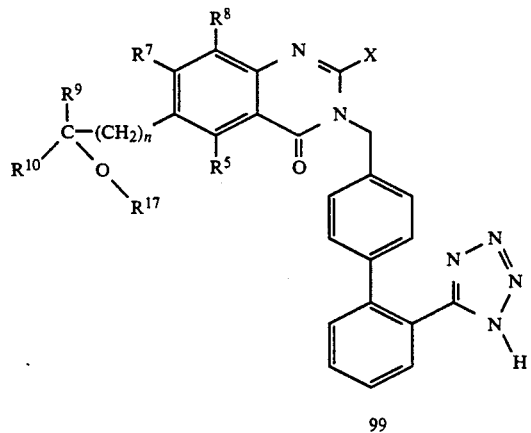

99

As shown in Scheme VII, alcohol 93 is reacted with an alkylating agent $R^{17}I$, wherein $R^{17}$ is alkyl of 1 to 4 carbon atoms, n is 0 to 3 and I is iodide, in the presence of a base, such as sodium hydride, to afford ethers 98. The intermediate ethers 98 are deblocked via dilute acid in acetone to give tetrazoles 99.

protecting group, is reacted with the desired acid anhydride, $(R^{17}CO)_2O$ wherein $R^{17}$ is defined as straight or branched lower alkyl of 1 to 4 carbon atoms or an acid chloride $R^{17}COCl$ where n is 0 to 3 in the presence of a base such as pyridine to afford ester 101.

Alcohol 93, is prepared via methods of Schemes I, II

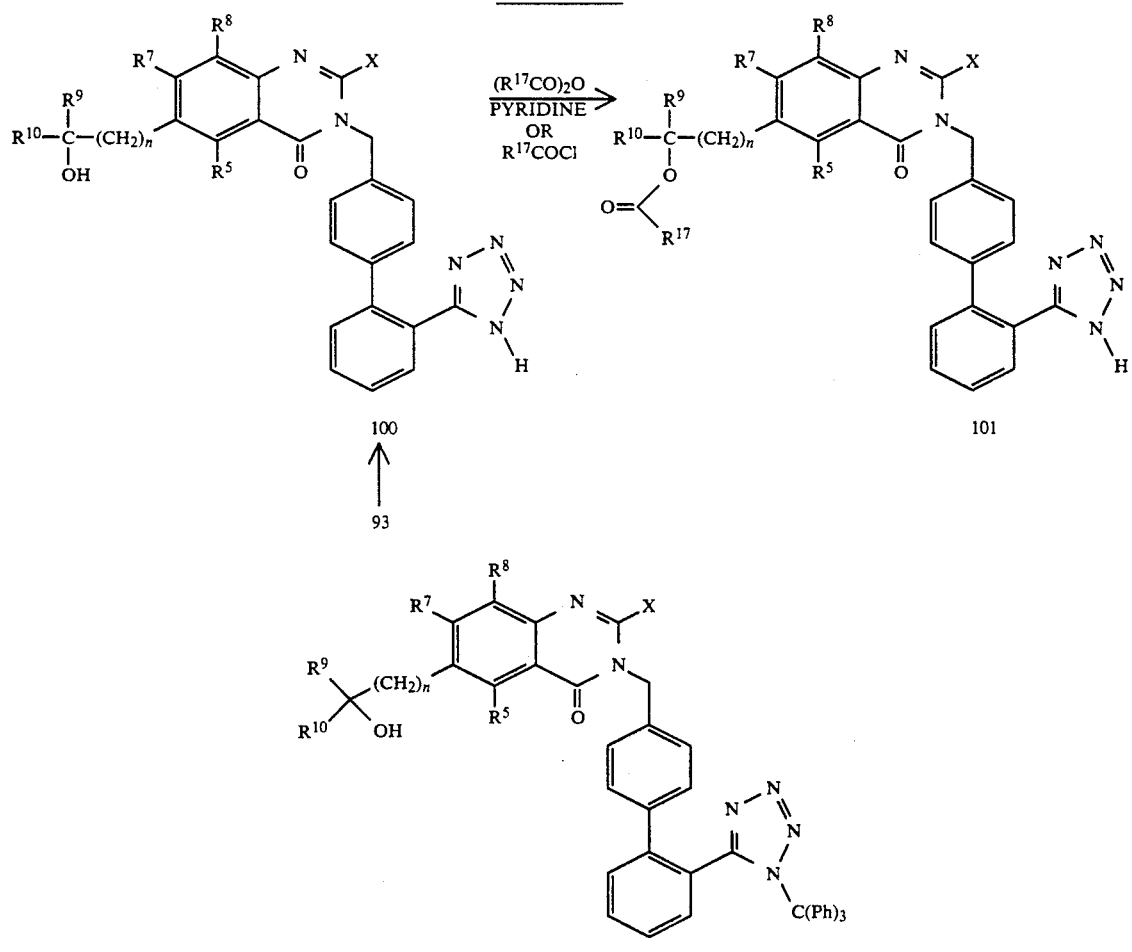

Alcohol 100, as shown in Scheme VIII, is prepared from 93 by dilute acid hydrolysis to remove the trityl and XV.

An alternate synthetic method of preparing 87 from 5 is illustrated in Scheme IX.

Scheme IX

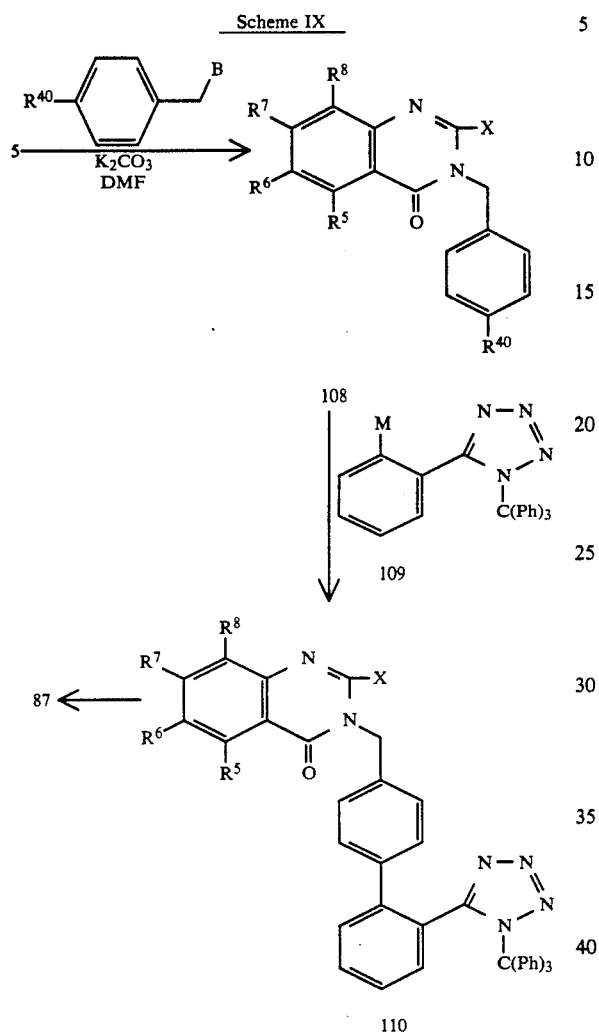

Quinazolinone 5 is alkylated in a solvent such as acetone in the presence of potassium carbonate with

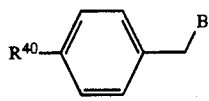

wherein $R^{40}$ is selected from I, Br or $-OSO_2CF_3$ and B is selected from appropriate leaving groups such as I, Br, Cl, $-OMs$, $-OTs$ or $-OSO_2CF_3$ to give 108. Palladium or nickel catalyzed coupling of 108 with 109 where M can be $-MgBr$, $-Sn$(lower alkyl of 1 to 4 carbon atoms or phenyl), Li or $-Zn$ complex, affords 110 which is deprotected to give 87.

Scheme X illustrates the method of preparing 109. Reaction of o-bromobenzonitrile with tri-n-butyltin azide affords 111. Further reaction of 111 with hydrogen chloride and trityl chloride gives 112. Reaction of 112 with a metal M such as magnesium, or n-BuLi or s-BuLi followed by $ZnCl_2$ or $(Me)_3SnCl$ affords 109.

Scheme X

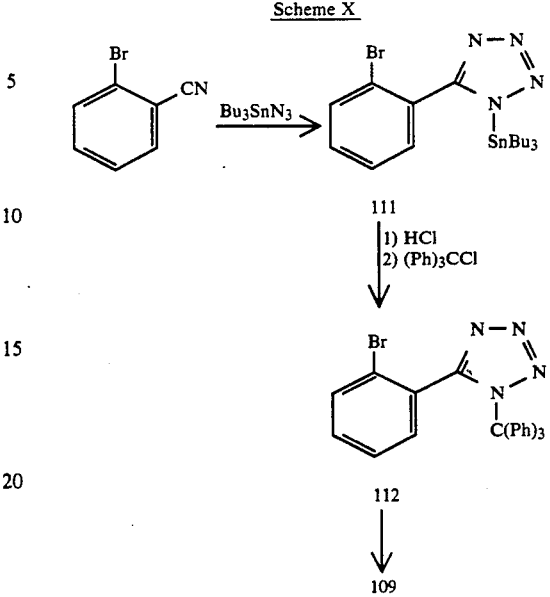

It will be appreciated that the chemical manipulations of $R^5$, $R^6$, $R^7$ and $R^8$ as outlined in Schemes I-X can be accomplished after alkylation as outlined in Scheme V. Additionally, it will also be appreciated that the chemical manipulations of $R^5$, $R^6$, $R^7$ and $R^8$ as outlined in Schemes VII-VIII can be accomplished before alkylation as outlined in Scheme V. The reactions are performed in a solvent appropriate to the reagents and materials em-ployed and suitable for the transformation being effected. It is understood by those skilled in the art of organic synthesis that the various functionalities present on the molecule must be consistent with the chemical transformations proposed. This will frequently necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Some of the compounds of the hereinbefore described Schemes have centers of asymmetry. The compounds may, therefore, exist in at least two and often four stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray cyrstallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation can be understood further by the following examples, but should not constitute a limitation thereof.

EXAMPLE 1

2-Butyl-6-(methyl)-4(1H)-quinazolinone

Method A

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolone as a white solid.

Method B:

The procedure described by B. Baker et. al., *J. Org. Chem.* 17 157(1952) and Sandmeyer, *Helv. Chim. Acta* 2, 234(1919) is used.

Examples 2-34 in Table 1 are prepared by using the appropriately substituted anthranilic acids by using synthetic method A or B described hereinabove.

TABLE I

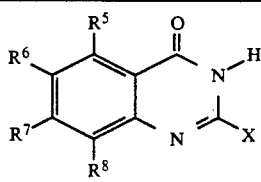

| Ex. No. | $R^5$ | $R^6$ | $R^7$ | $R^8$ | X | Synthesis Method | MP °C. |
|---|---|---|---|---|---|---|---|
| 2 | H | Br | H | H | $-(CH_2)_3CH_3$ | A | 111 |
| 3 | H | H | H | H | $-(CH_2)_3CH_3$ | A | 129 |
| 4 | H | Cl | H | H | $-(CH_2)_3CH_3$ | A | 194 |
| 5 | H | I | H | H | $-(CH_2)_3CH_3$ | A | 257-258 |
| 6 | H | I | H | I | $-(CH_2)_3CH_3$ | A | 267-268 |
| 7 | H | $CH_3$ | H | H | $-(CH_2)_3CH_3$ | A | 231-232 |
| 8 | H | Cl | H | H | $-(CH_2)_3CH_3$ | A | 255-256 |
| 9 | H | H | H | H | $-(CH_2)_3CH_3$ | A | 185-187 |
| 10 | H | $CH_3$ | H | H | $-(CH_2)_3CH_3$ | A | * |
| 11 | H | $OCH_3$ | H | H | $-(CH_2)_3CH_3$ | B | 181-182° C. |
| 12 | H | Cl | H | H | $-(CH_2)_3CH_3$ | A | 194° C. |

*CI MASS SPEC MH+ 217

EXAMPLE 13

2-Butyl-7-carboethoxy-4(1H)-quinazolinone

A mixture of 5.0 g of 2-butyl-7-carboxy-4(1H)-quinazolinone in 100 ml of absolute ethanol containing 2 ml of sulfuric acid is refluxed for 48 hours. The solvent is evaporated in vacuo and the residue partitioned between water and chloroform. The organic layer is washed with aqueous saturated sodium bicarbonate, dried with anhydrous sodium sulfate, filtered and evaporated to a residue which crystallizes from ethyl acetate-hexane to afford 4.5 g of the desired product, mp 145° C.

EXAMPLE 14

2-Butyl-6-(bromomethyl)-4(1H)-quinazolinone

To a suspension of 3.50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl quinazolinone is obtained and used in the next step without further purification.

EXAMPLE 15

2-Butyl-6-(hydroxymethyl)-4(1H)-quinazolinone

To a suspension of 2.0 g of impure 2-butyl-6-(bromomethyl)-4(1H)-quinazolinone in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid. CI MASS SPEC 233(M+H).

EXAMPLE 16

2-Butyl-1,4-dihydro-4-oxo-6-quinazoline-carboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(M+H).

EXAMPLE 17

2-Butyl-6-(1-hydroxyethyl)-4(1H)-quinazolinone

To a solution of 0.60 g of 2-butyl-1,4-dihydro-4-oxo-6-quinazoline-carboxaldehyde in 30 ml of dry tetrahydrofuran, cooled to 0° C. is added dropwise, 2.61 ml of a 3.0M solution of methylmagnesium bromide in diethyl ether. The reaction is stirred at 0° C. for 30 minutes and then quenched with 10 ml of aqueous ammonium chloride. After diluting with 10 ml of water, the reaction mixture is extracted with 9:1 chloroform-methanol. The combined extracts are dried with magnesium sulfate, filtered and concentrated to yield 0.64 g of the desired product. CI MASS SPEC 247(MH+).

EXAMPLE 18

2-Butyl-6-(1-hydroxypropyl)-4(1H)-quinazolinone

To a solution of 0.25 g of 2-butyl-1,4-dihydro-4-oxo-6-quinazoline-carboxaldehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 19

2-Butyl-1,4dihydro-4-oxo-6-quinazoline-carboxaldehyde

To a solution of 1.0 g of 2-butyl-1,4-dihydro-4-oxo-6-iodo-quinazoline and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°–244° C.

EXAMPLE 20

2-Butyl-6-[(trimethylsilyl)ethylnyl]-4(1H)-quinazolinone

To a solution of 1.0 g of 2-butyl-1,4-dihydro-4-oxo-6-iodo-quinazolinone 0.043 g of bis(triphenylphosphine)-palladium (II) chloride and 5.8 mg of copper (I) iodide in 5.0 ml of N,N-dimethylformamide and 5.0 ml of triethylamine is added 0.36 g of (trimethylsilyl)acetylene. The resulting reaction mixture is heated at 45° C. for 1 hour and them 65° C. for 5 hours. Upon cooling, the reation mixture is concentrated in vacuo and the residue is purified by flash chromatography on silica gel, eluting with 1:3 ethyl acetate-hexane to yield 0.75 g of the desired product as a white solid. CI MASS SPEC 299(M+).

EXAMPLE 21

2-Butyl-6-[(trimethylsilyl)ethylnyl]-7-fluoro-4(1H)-quinazolinone

The compound is prepared using the experimental conditions of Example 20 starting from 7-fluoro-6-bromo-2-butyl-4(1H)-quinazolinone, m.p 192° C.

EXAMPLE 22

2-Butyl-6-ethylnyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product. CI MASS SPEC 227(MH+).

EXAMPLE 23

6-Acetyl-2-butyl-4(1H)-quinazolinone

To a solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid. CI MASS SPEC 245(MH+).

EXAMPLE 24

2-Butyl-6-(1-hydroxy-1-methylethyl)-4(1H)-quinazolinone

To a solution of 4.00 g 6-acetyl-2-butyl-4(1H)-quinazolinone in 250 ml of dry tetrahydrofuran, cooled to 0° C., is added dropwise 16.4 ml of 3.0M methylmagnesium bromide in diethyl ether. The reaction is stirred at 0° C. for 0.5 hours and then allowed to warm to room temperature followed by quenching with 100 ml of saturated ammonium chloride solution. The mixture is diluted with 50 ml of water and extracted with ethyl acetate. The combined organic layers are washed with brine, dried over anhydrous magnesium sulfate, filtered and concentrated in vacuo. The residue is purified by flash chromatography on silica gel, eluting with 100:0.25 chloroform-methanol to give 2.75 g of the desired product as a white solid. CI MASS SPEC 261(MH+).

EXAMPLE 25

2-Butyl-6-(1-hydroxyethyl)-4(1H)-quinazolinone

To a suspension of 0.102 g of 6-acetyl-2-butyl-4(1H)quinazolinone in 10.0 ml of ethanol is added 0.015 g of sodium borohydride. The reaction mixture is stirred for 1.5 hours at room temperature and then diluted with 50 ml of water. The aqueous layer is extracted with 5:1 chloroform-methanol and the combined organics dried over magnesium sulfate, filtered and concentrated in vacuo to yield 0.103 g of the desired product. CI MASS SPEC 247(MH+).

EXAMPLE 26

2-Butyl-6-ethyl-4(1H)-quinazolinone

To a suspension of 0.278 g of 2-butyl-6-ethynyl-4(1H)quinazolinone in 8 ml of pyridine is added 0.080 g of 5% palladium-on-barium sulfate. The reaction is stirred under a hydrogen atmosphere for 48 hours, filtered, concentrated in vacuo and the residue purified by flash chromatography on silica gel eluting with ethyl acetate-hexanes to give 0.179 g of the desired product. CI MASS SPEC 231(MH+).

EXAMPLE 27

Methyl 2-butyl-1,4-dihydro-4-oxo-6-quinazolinecarboxylate

To a solution of 1.00 g of 2-butyl-1,4-dihydro-4-oxo-6-iodoquinazoline and 6.0 ml of triethylamine in 25 ml of methanol and 5 ml of N,N-dimethylformamide is added 0.275 g of bis(triphenylphosphine)palladium (II) chloride. The reaction mixture is heated at reflux under an atmosphere of carbon monoxide for 16 hours, then allowed to cool and concentrated in vacuo. The residue is purified by flash chromatography on silica gel, eluting with 1:1 ethyl acetate-hexanes to give 0.389 g of the desired product as a white solid. CI MASS SPEC 261(MH+).

EXAMPLE 28

2-Butyl-6-(1-hydroxy-1-methylethyl)-4(1H)-quinazolinone

To a solution of 0.075 g of methyl 2-butyl-1,4-dihydro-4-oxo-6-quinazolinecarboxylate in 5 ml of dry tetrahydrofuran, cooled to 0° C., is added dropwise 0.51 ml of a solution of 3.0M methylmagnesium bromide in diethyl ether. The reaction is stirred at 0° C. for 0.5 hours and then at room temperature for 1 hour followed by quenching with 10 ml of saturated ammonium chloride solution. The resulting reaction mixture is diluted with 10 ml of water and extracted with ethyl acetate. The combined organics are dried over magnesium sulfate, filtered and concentrated in vacuo. The residue is purified by flash chromatography on silica gel, eluting with 100:0.25 chloroform-methanol to yield 0.055 g of the desired product as a white solid, m.p. 190°–192° C.

EXAMPLE 29

2-Butyl-6-(1-methylethenyl)-4(1H)-quinazolinone

To a suspension of 3.66 g of methyltriphenylphosphonium bromide in 30 ml of dry tetrahydrofuran, cooled to −78° C., is added dropwise 5.9 ml of a 1.73M solution of n-butyllithium in hexanes. Following complete addition, the reaction mixture is allowed to warm to room temperature and stirred for 15 minutes, until all the phosphonium bromide is dissolved. The reaction mixture is then recooled to −78° C. and a suspension of 6-acetyl-2-butyl-4(1H)-quinazolinone in 15 ml of dry tetrahydrofuran is added. The reaction is allowed to warm to room temperature and stirred for 24 hours followed by quenching with saturated ammonium chloride solution. After diluting with 10 ml of water, the aqueous layer is extracted with chloroform and the combined organics dried over magnesium sulfate, filtered and concentrated in vacuo. The residue is purified by flash chromatography on silica gel, eluting with 1:2 ethyl acetate-hexanes to give 0.23 g of the desired product as a white solid. CI MASS SPEC 243(MH+).

EXAMPLE 30

2-Butyl-6-(hydroxyphenylmethyl)-4(1H)-quinazolinone

To a stirred solution of 2.00 g of 2-butyl-1,4-dihydro-4-oxo-6-quinazoline-carboxaldehyde in 100 ml of tetrahydrofuran, cooled at 0° C., is added 13.0 ml of 2.0M phenyllithium and stirring continued for 1 hour. The cooling is removed and the reaction allowed to reach room temperature followed by an additional 30 minutes at room temperature. The reaction is diluted with saturated ammonium chloride solution and extracted with ethyl acetate. The organic layer is dried, evaporated to a residue, which is purified by chromatography on silica gel by elution with 0.25:100 methanol-chloroform to give 0.932 g of the desired product. CI MASS SPEC 309(MH+).

EXAMPLE 31

2-Butyl-6-(1-hydroxyethyl)-3-[[2'-[1-(triphenylmethyl)-1H-tetrazol-5-yl][1,1'-biphenyl]-4-yl]methyl]-4(3H)-quinazolinone A suspension of 2.50 g of 2-butyl-6-(1-hydroxyethyl)-4(1H)-quinazolinone, 6.79 g of 5-[4'-(bromomethyl)[1,1'-biphenyl]-2-yl]-1-(triphenylmethyl)-1H-tetrazole and 4.20 g of anhydrous potassium carbonate in 225 ml of dry acetone is heated at reflux for 16 hours. The reaction mixture is allowed to cool to room temperature, filtered and the filtrate evaporated in vacuo. The residue is purified by high pressure liquid chromatography on silica gel by eluting with 1:2 ethyl acetate-hexanes to afford 4.25 g of the desired product as a white solid, FAB M+H 723.

Examples 32–48 in Table II are prepared under substantially the same alkylation conditions as Example 31 from the appropriately substituted quinazolinone starting materials.

TABLE II

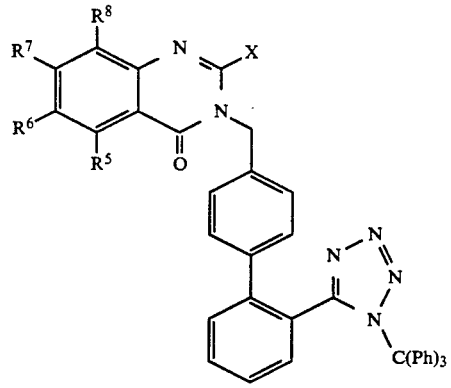

| Ex. No. | $R^5$ | $R^6$ | $R^7$ | $R^8$ | X | FAB Low Resolution Mass Spectrum |
|---|---|---|---|---|---|---|
| 32 | H | —CH(OH)CH₃ | H | H | —(CH₂)₃CH₃ | 723(M + H) |
| 33 | H | CH₃ | H | H | —(CH₂)₃CH₃ | 693(M + H) |
| 34 | H | —CH₂CH₃ | H | H | —(CH₂)₃CH₃ | 707(M + H) |
| 35 | H | —CH₂OH | H | H | —(CH₂)₃CH₃ | 709(M + H) |
| 36 | H | H | H | H | —(CH₂)₃CH₃ | 665(M + H) |
| 37 | H | —CH(OH)CH₂CH₃ | H | H | —(CH₂)₃CH₃ | 737(M + H) |
| 38 | H | —(CH₃)₂OH | H | H | —(CH₂)₃CH₃ | 737(M + H) |
| 39 | H | CH₃ | H | H | —(CH₂)₃CH₃ | 693(M + H) |
| 40 | H | H | H | H | —(CH₂)₃CH₃ | 665(M + H) |
| 41 | H | —CO₂CH₃ | H | H | —(CH₂)₃CH₃ | 737(M + H) |

TABLE II-continued

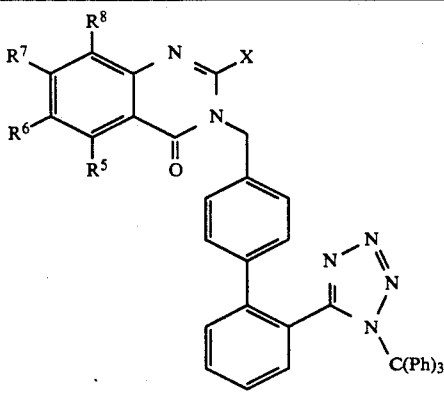

| Ex. No. | R⁵ | R⁶ | R⁷ | R⁸ | X | FAB Low Resolution Mass Spectrum |
|---|---|---|---|---|---|---|
| 42 | H | —C(O)—CH₃ | H | H | —(CH₂)₃CH₃ | 721(M + H) |
| 43 | H | —CH(OCH₃)CH₃ | H | H | —(CH₂)₃CH₃ | 737(M + H) |
| 44 | H | —CH(OCH₃)C₆H₅ | H | H | —(CH₂)₃CH₃ | 799(M + H) |
| 45 | H | —CH(OH)C₆H₅ | H | H | —(CH₂)₃CH₃ | 807(M + Na) |
| 46 | H | —CH(OCH₃)C₂H₅ | H | H | —(CH₂)₃CH₃ | 751(M + H) |
| 47 | H | —C(CH₃)₂OCH₃ | H | H | —(CH₂)₃CH₃ | 751(M + H) |
| 48 | H | Cl | H | H | —(CH₂)₃CH₃ | 609(M + H) |

EXAMPLE 49

2-Butyl-6-(1-hydroxyethyl)-3-[[2'-(1H-tetrazol-5-yl)-[1,1'-biphenyl]-4-yl]methyl]-4(3H)-quinazolinone To a suspension of 2.00 g of 2-butyl-6-(1-hydroxyethyl)-3-[[2'-[1-(triphenylmethyl)-1H-tetrazol-5-yl][1,1'biphenyl]-4-yl]methyl]-4(3H)-quinazolinone in 70 ml of 3:1 acetone-water is added one drop of 5% aqueous hydrochloric acid solution. The mixture is then heated at reflux for 16 hours. After cooling, the reaction mixture is concentrated in vacuo and the residue purified by flash chromatography on silica gel by elution with 9:1 chloroform-methanol to afford 0.915 g of the desired product as a white solid, m.p. 146°–147° C.

Examples 50–57 in Table III are prepared under substantially the same conditions as Example 49 from the appropriately substituted quinazolinone starting materials.

TABLE III

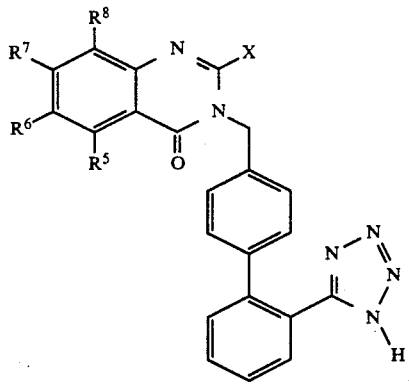

| Ex. No. | R⁵ | R⁶ | R⁷ | R⁸ | X | MP °C. | FAB MS |
|---|---|---|---|---|---|---|---|
| 50 | H | H | H | H | —(CH₂)₃CH₃ | 92 | |
| 51 | H | —C(CH₃)₂OH | H | H | —(CH₂)₃CH₃ | 156–158 | |
| 52 | H | —CH(OH)CH₂CH₃ | H | H | —(CH₂)₃CH₃ | 138–140 | |
| 53 | H | —CH₂OH | H | H | —(CH₂)₃CH₃ | 126–128 | |
| 54 | H | —CH(OH)C₆H₅ | H | H | —(CH₂)₃CH₃ | | 543(M + H) |
| 55 | H | —CH(OCH₃)C₂H₅ | H | H | —(CH₂)₃CH₃ | | 509(M + H) |
| 56 | H | —C(C₆H₅)OCH₃ | H | H | —(CH₂)₃CH₃ | | 557(M + H) |
| 57 | H | —C(CH₃)₂OCH₃ | H | H | —(CH₂)₃CH₃ | | 509(M + H) |

EXAMPLE 58

6-[1-(Acetyloxy)ethyl]-2-butyl-3-[[2'-(1H-tetrazol-5-yl)[1,1'-biphenyl]-4-yl]methyl]-4(3H)-quinazolinone To a solution of 1.00 g of 2-butyl-6-(1-hydroxyethyl)-3-[[2'-(1H-tetrazol-5-yl)-[1,1'-biphenyl]4-yl]methyl-4(3H)-quinazolinone in 2.0 ml of acetic anhydride at room temperature is added 2 drops of dry pyridine. The reaction is stirred at room temperature for 16 hours then evaporated in vacuo. The residue is purified by flash chromatography on silica gel eluting with 95:5 chloroform-methanol to yield 0.059 g of the desired product as a white solid. FAB MASS SPEC 523(M+H).

EXAMPLE 59

2-Butyl-6-(1-methoxyethyl)-4-[[2'-(1H-tetrazol)-5-yl)[1,1'-biphenyl]-4-yl]methyl]-4(3H)-quinazolinone A mixture of 0.300 g of 2-butyl-6-(1-methoxyethyl)-3-[[2'-[1-(triphenylmethyl)-1H-tetrazol-5-yl]-[1,1'-biphenyl]-4-yl]methyl-4(3H)-quinazolinone in 20 ml of 3:1 acetone-water containing 1 drop of 5% hydrochloric acid is heated at reflux for 16 hours and evaporated to a residue. The residue is purified on silica gel eluting with 95.5 chloroform-methanol to provide 0.171 g of the product as a white solid, mp 154°–156° C.

EXAMPLE 60

2-Butyl-6-(1-methoxyethyl)-3-[[2'-[1-(triphenylmethyl)-1H-tetrazol)-5-yl][1,1'-biphenyl]-4-yl]methyl-4(3H)-quinazolinone To a suspension of 0.044 g of a 60% dispersion of sodium hydride in mineral oil and 0.345 ml of methyl iodide in 5.0 ml of dry tetrahydrofuran at room temperature is added 0.400 g of 2-butyl-6-(1-hydroxyethyl)-3-[[2'-[1-(triphenylmethyl)-1H-tetrazol-5-yl]-[1,1'-biphenyl]-4-yl]methyl]-4(3H)-quinazolinone in one portion. The reaction is stirred at room temperature for 18 hours and then poured onto a pad of silica gel. Elution with 1:3 ethyl acetate-hexanes and fractions containing the desired product evaporated to provide 0.356 g of a white solid. FAB MASS SPEC 737(M+H).

EXAMPLE 61

2-Butyl-6-(1-hydroxy-1-methylethyl)-3-[[2'-(1H-tetrazol-5-yl)[1,1'-biphenyl]-4-yl]methyl]-4(3H)-quinazolinone monosodium salt A mixture of 0.400 g of 2-Butyl-6-(1-hydroxy-1-methylethyl)-3-[[2'-(1H-tetrazol-5-yl)[1,1'-biphenyl]-4-yl]methyl]-4(3H)-quinazolinone monosodium salt, 10 ml of methanol and 0.810 ml of 1N sodium hydroxide is stirred at room temperature for 1 hour and evaporated in vacuo to a residue which is triturated with ether, filtered and the cake air dried to give the desired product as a solid. FAB MASS SPEC 517(M+H).

EXAMPLE 62

2-Butyl-6-(hydroxymethyl)-3-[[2'-(1H-tetrazol-5-yl)[1,1'-biphenyl]-4-yl]methyl]-4(3H)-quinazolinone monosodium salt Following the procedure of Example 182 and using 2-Butyl-6-(1-hydroxy-1-methylethyl)-3-[[2'-(1H-tetrazol-5-yl)[1,1'-biphenyl]-4-yl]methyl]-4(3H)-quinazolinone affords the product of the Example.

EXAMPLE 63

2-Butyl-6-(1-methoxy-1-methylethyl)-3-[[2'-[1-(triphenylmethyl)-1H-tetrazol-5-yl][1,1'-biphenyl]-4-yl]methyl-4(3H)-quinazolinone To a suspension of 0.049 g of a 60% oil dispersion of sodium hydride in 4.5 ml of THF is added 0.76 ml of methyl iodide followed by 0.45 g of 2-butyl-6-(1-hydroxy-1-methylethyl)-3-[[2'-(1H-tetrazol-5-yl)-[1,1'-biphenyl]-4-yl]methyl]-4(3H)-quinazolinone. The reaction mixture is stirred at room temperature for 24 hours and then an additional 0.05 g of 60% sodium hydride and 0.80 ml of methyl iodide are added. The reaction is stirred at room temperature for another 24 hours and then quenched with saturated ammonium chloride solution and extracted with ether. The organics are dried over MgSO₄, filtered and concentrated in vacuo. The residue is purified by flash chromatography on silica gel, eluting with 1:5 ethyl acetate/hexanes to provide 0.397 g of the desired product as a white solid. FAB MASS SPEC 751(M+H).

EXAMPLE 64

2-Butyl-6-(1-methoxy-1-methylethyl)-3-[[2'-(1H-tetrazol-5-yl)[1,1'-biphenyl]-4-yl]methyl]-4(3H)-quinazolinone The product of the Example is prepared using the conditions of Example 111 and 0.397 g of 2-Butyl-6-(1-methoxy-1-methylethyl)-3-[[2'-[1-(triphenylmethyl)-1H-tetrazol-5-yl][1,1'-biphenyl]-4-yl]methyl]-4(3H)-quinazolinone to give 0.188 g of the desired product as a white solid following chromatography on silica gel by elution with 50:50:5:0.1 ethyl acetate/hexanes/methyl alcohol/acetic acid. FAB MASS SPEC 509(M+H).

EXAMPLE 65

2-Butyl-6-(methoxyphenylmethyl)-3-[[2'-[1-(triphenylmethyl)-1H-tetrazol-5-yl][1,1'-biphenyl]-4-yl]methyl]-(3H)-quinazolinone To a solution of 0.398 ml of methyl iodide in 5.0 ml of THF is added 0.851 g of 60% sodium hydride followed by 0.500 g of 2-butyl-6-(hydroxyphenylmethyl)-3-[[2'-[1-(triphenylmethyl)-1H-tetrazol-5-yl][1,1'-biphenyl]-4-yl]methyl]-4(3H)-quinazolinone. The reaction mixture is stirred for 16 hours at room temperature, then quenched with saturated NH₄Cl solution and extracted with ether. The organics are dried over MgSO₄, filtered and concentrated in vacuo. The residue is purified by flash chromatography on silica gel, eluting with ethyl acetate/hexanes (1:5) to provide 0.434 g of FAB MASS SPEC 799(M+H).

EXAMPLE 66

2-Butyl-6-(methoxyphenylmethyl)-3-[[2'-(1H-tetrazol-5-yl)[1,1'-biphenyl]-4-yl]methyl]-4(3H)-quinazolinone The product of the Example is prepared using the conditions of Example 49 and 0.413 g of 2-Butyl-6-(methoxyphenylmethyl)-3-[[2'-[1-(triphenylmethyl)-1H-tetrazol-5-yl][1,1'-biphenyl]-4-yl]methyl]-(3H)-quinazolinone to give 0.192 g of the desired product as a white solid following chromatography on silica gel by elution with 50:50:5:0.1 ethyl acetate/hexanes/methyl alcohol/acetic acid. FAB MASS SPEC 557(M+H).

EXAMPLE 67

2-Butyl-6-(1-methoxypropyl)-3-[[2'-[1-(triphenylmethyl)-1H-tetrazol-5-yl][1,1'-biphenyl]-4-yl]methyl]-4(3H)-quinazolinone To a solution of 0.556 ml of methyl iodide in 5.0 ml of THF is added 0.071 g of 60% sodium hydride followed by 0.657 g of 2-butyl-6-(1-hydroxypropyl)-3-[[2'-[1-(triphenylmethyl)-1H-tetrazol-5-yl][1,1'-biphenyl]-4-yl]methyl]4(3H)-quinazolinone. The reaction is stirred for 16 hours at room temperature, then quenched with saturated NH₄Cl solution and extracted with ether. The organics are dried over MgSO₄, filtered and concentrated in vacuo. The residue is purified by flash chromatography on silica gel, eluting with 1:5 ethyl acetate/hexanes to provide 0.59 g of the desired product as a white solid. FAB MASS SPEC 751(M+H).

EXAMPLE 68

2-Butyl-6-(1-methoxypropyl)-3-[[2'-(1H-tetrazol-5-yl)[1,1'-biphenyl]-4-yl]methyl]-4(3H)-quinazolinone The product of the Example is prepared using the conditions of Example 111 and 0.58 g of 2-Butyl-6-(1-methoxypropyl)-3-[[2'-[1-(triphenylmethyl)-1H-tetrazol-5-yl][1,1'-biphenyl]-4-yl]methyl]-4(3H)-quinazolinone to give 0.326 g of the desired product as a white solid following chromatography on silica gel by elution with 50:50:5:0.1 ethyl acetate/hexanes/methyl alcohol/acetic acid. FAB MASS SPEC 509(M+H).

EXAMPLE 69

1-Amino-3-fluoro-4-bromo-benzoic acid

To a solution of 3.0 g of 4-fluoroanthranilic acid in 250 ml of glacial acetic acid is slowly added a solution of 3.2 g of bromine in 10 ml of acetic acid. The reaction mixture is stirred at room temperature for 8 hours and poured into 500 ml of water. The resulting precipitate is filtered off and the cake crystallized from methyl alcohol to give 3.4 g of the desired product, m.p. 180°.

EXAMPLE 70

6-Bromo-2-butyl-7-fluoro-4(1H)-quinazolinone

Following the procedure of Example 1 and using 3.0 g of 1-amino-3-fluoro-4-bromo-benzoic acid, 100 ml of valeric anhydride and 200 ml of ammonium hydroxide affords the product of the Example, m.p. 225° C.

EXAMPLE 71

2-Butyl-7-fluoro-6-[(trimethylsilyl)ethynyl]-4(1H)-quinazolinone

Using the procedure of Example 20 and 6-bromo-2-butyl-7-fluoro-4(1H)-quinazolinone, the product of the Example is obtained, m.p. 192° C.

EXAMPLE 72

2-Butyl-6-ethynyl-7-fluoro-4(1H)-quinazolinone

A mixture of 1.0 g of 2-butyl-7-fluoro-6-[(trimethylsilyl)ethynyl]-4(1H)-quinazolinone, 20 ml of 1N sodium hydroxide and 25 ml of methyl alcohol is heated at 60° C. for 5 hours then evaporated in vacuo. The residue is dissolved in 100 ml of water and acidified. The resulting solid is collected and dried to afford 700 mg of the desired product as a yellow solid, m.p. 218° C.

EXAMPLE 73

3-[(4-Bromophenyl)methyl]-2-butyl-6-(1-hydroxy-1-methylethyl)-4(3H)-quinazolinone To a solution of 1.37 g of 2-butyl-6-(1-hydroxy-1-methylethyl)-4(1H)-quinazolinone in 115 ml of acetone is added 1.58 g of 4-bromobenzyl bromide and 2.18 g of anhydrous potassium carbonate. The resulting suspension is heated to reflux for 16 hours. The reaction mixture is then allowed to cool to room temperature, filtered and the filtrate is concentrated vacuo. The residue is purified by HPLC eluting with ethyl acetate/hexanes (1:3) to provide the desired product.

Examples 74-84 in Table VI are prepared under substantially the same alkylation conditions as Example 73 from the appropriately substituted quinazolinone starting materials.

TABLE VI

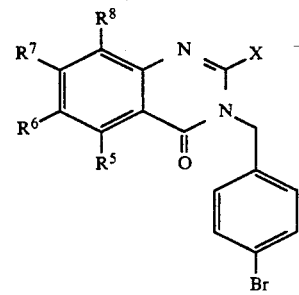

| Ex. No. | $R^5$ | $R^6$ | $R^7$ | $R^8$ | X |
|---|---|---|---|---|---|
| 74 | H | I | H | H | —(CH₂)₃CH₃ |
| 75 | H | —CH(OH)CH₃ | H | H | —(CH₂)₃CH₃ |
| 76 | H | CH₃ | H | H | —(CH₂)₃CH₃ |
| 77 | H | —CH₂OH | H | H | —(CH₂)₃CH₃ |
| 78 | H | H | H | H | —(CH₂)₃CH₃ |
| 79 | H | —CH(OH)CH₂CH₃ | H | H | —(CH₂)₃CH₃ |
| 80 | H | —C(CH₃)₂OH | H | H | —(CH₂)₃CH₃ |
| 81 | H | CH₃ | H | H | —(CH₂)₃CH₃ |
| 82 | H | H | H | H | —(CH₂)₃CH₃ |
| 83 | H | —CH(OH)C₆H₅ | H | H | —(CH₂)₃CH₃ |
| 84 | H | Cl | H | H | —(CH₂)₃CH₃ |

EXAMPLE 85

3-[(4-Bromophenyl)methyl]-2-butyl-6-(1-methoxy-1-methylethyl)-4(3H)-quinazolinone To a solution of 0.186 g of 60% sodium hydride and 2.90 ml of iodomethane in THF at room temperature is added 1.00 g of 3-[(4-bromophenyl)methyl]-2-butyl-6-(1-hydroxy-1-methylethyl)-4(3H)-quinazolinone. The reaction mixture is stirred overnight at room temperature and then quenched with ammonium chloride solution and diluted with water. The aqueous layer is extracted with ether and the combined organics are dried over MgSO₄, filtered and concentrated in vacuo. The residue is purified by flash chrmoatography eluting with ethyl acetate/hexanes (1:3) to provide the desired product.

Examples 86–89 in Table VII are prepared under substantially the same alkylation conditions as Example 85 from the appropriately substituted quinazolinone starting materials.

TABLE VII

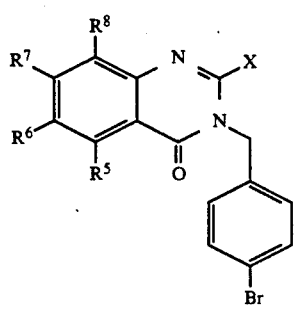

| Ex. No. | R⁵ | R⁶ | R⁷ | R⁸ | X |
|---|---|---|---|---|---|
| 86 | H | —CH(OCH₃)CH₃ | H | H | —(CH₂)₃CH₃ |
| 87 | H | —CH(OCH₃)C₆H₅ | H | H | —(CH₂)₃CH₃ |
| 88 | H | —CH(OCH₃)C₂H₅ | H | H | —(CH₂)₃CH₃ |
| 89 | H | —C(CH₃)₂OCH₃ | H | H | —(CH₂)₃CH₃ |

EXAMPLE 90

2-Butyl-6-(1-methoxy-1-methylethyl)-3-[[2'-[1-(triphenylmethyl)-1H-tetrazol-5-yl][1,1'-biphenyl]-4-yl]methyl]-4(3H)-quinazolinone To a suspension of 0.41 g of magnesium turnings in 50 ml of THF is added a catalytic amount of iodine followed by 1.00 g of the 5-(2-bromophenyl)-1-(triphenylmethyl)-1H-tetrazole in 10 ml of THF. The reaction mixture is heated to reflux until the Grignard formation is initiated as indicated by the disappearance of the iodine color. The remaining 6.94 g of the bromide in 70 ml of THF is then added to the reaction at a rate sufficient to maintain a gentle reflux. The reaction is then stirred at room temperature for 4 hours following the completion of the bromide addition.

To a solution of 4.08 g of the 3-[(4-bromophenyl)methyl]-2-butyl-6-(1-methoxy-1-methylethyl)-4(3H)-quinazolinone and 71 mg of 1,4-bis(diphenylphosphino)butane palladium (II) chloride in 100 ml of THF is added the Grignard solution described above and the resulting solution is heated to reflux for 2 hours, following the method of Kumada (*Tet. Letters*, 52, 5319 (1981). After cooling to room temperature, the reaction is quenched with water and dilute sodium hydroxide solution and then extracted with ether. The combined organics are dried over MgSO₄, filtered and concentrated in vacuo. The residue is purified by flash chromatography on silica gel eluting with ethyl acetate/hexanes (1:3) to provide the desired product.

EXAMPLES 91–94 in Table VIII are prepared under substantially the same coupling conditions as Example 90 from the appropriately substituted quinazolinone starting materials.

TABLE VIII

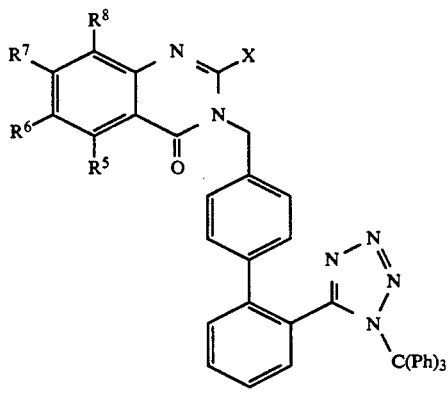

| Ex. No. | R⁵ | R⁶ | R⁷ | R⁸ | X |
|---|---|---|---|---|---|
| 91 | H | —CH(OCH₃)CH₃ | H | H | —(CH₂)₃CH₃ |
| 92 | H | —CH(OCH₃)C₆H₅ | H | H | —(CH₂)₃CH₃ |
| 93 | H | —CH(OCH₃)C₂H₅ | H | H | —(CH₂)₃CH₃ |
| 94 | H | —C(CH₃)₂OCH₃ | H | H | —(CH₂)₃CH₃ |

EXAMPLE 95

3-[(4-Bromophenyl)methyl]-2-butyl-6-[1-[[(1,1-dimethylethyl)dimethylsilyl]oxy]-1-methylethyl]-4(3H)-quinazolinone To a solution of 1.00 g of 3-[(4-bromophenyl) methyl]-2-butyl-6-(1-hydroxy-1-methylethyl)-4(3H)-quinazolinone in 2.0 ml of DMF is added 0.438 g of t-butyldimethylsilyl chloride followed by 0.4 g of imidazole. The reaction mixture is stirred at room temperature for 18 hours and then diluted with water and extracted with ether. The combined ether extracts are dried over MgSO₄, filtered and concentrated in vacuo. The residue was purified by flash chromatography eluting with ethyl acetate/hexanes (1:5) to provide the desired product as a white solid.

Examples 96–100 in Table IX are prepared under substantially the same conditions as Example 95 from the appropriately substituted quinazolinone starting materials.

TABLE IX

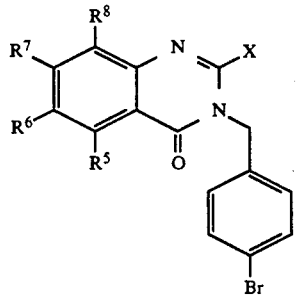

| Ex. No. | R⁵ | R⁶ | R⁷ | R⁸ | X |
|---|---|---|---|---|---|
| 96 | H | —CH(OTBDMS)CH₃ | H | H | —(CH₂)₃CH₃ |
| 97 | H | —CH₂OTBDMS | H | H | —(CH₂)₃CH₃ |
| 98 | H | —CH(OTBDMS)CH₂CH₃ | H | H | —(CH₂)₃CH₃ |
| 99 | H | —C(CH₃)₂OTBDMS | H | H | —(CH₂)₃CH₃ |

TABLE IX-continued

[Structure: benzene ring with R^7, R^8, R^6, R^5 substituents, fused to N=C(X)–N(CH2-C6H4-Br)–C(=O) ring]

| Ex. No. | R^5 | R^6 | R^7 | R^8 | X |
|---|---|---|---|---|---|
| 100 | H | —CH(OTBDMS)C$_6$H$_5$ | H | H | —(CH$_2$)$_3$CH$_3$ |

*TBDMS = t-butyldimethylsilyl

EXAMPLE 101

2-Butyl-6-[1-[[(1,1-dimethylethyl]dimethylsilyl]oxy]-1-methylethyl]-3-[[2'-[1-(triphenylmethyl)-1H-tetrazol-5-yl][1,1'-biphenyl]-4-yl]methyl]-4(3H)-quinazolinone To a suspension of 0.41 g of magnesium turnings in 50 ml of THF is added a catalytic amount of iodine followed by 1.00 g of the 5-(2-bromophenyl)-1-(triphenylmethyl)-1H-tetrazole in 10 ml of THF. The reaction mixture is heated to reflux until the Grignard formation is initiated as indicated by the disappearance of the iodine color. The remaining 6.94 g of the bromide in 70 ml of THF is then added to the reaction at a rate sufficient to maintain a gentle reflux. The reaction is then stirred at room temperature for 4 hours following the completion of the bromide addition.

To a solution of 5.00 g of 3-[(4-bromophenyl) methyl]-2-butyl-6-[1-[[(1,1-di-methylethyl)dimethylsilyl]oxy]-1-methylethyl]-4(3H)-quinazolinone and 71 mg of 1,4-bis(diphenylphosphino)butane palladium (II) chloride in 100 ml of THF is added the Grignard solution described above and the resulting solution is heated to reflux for 2 hours, fillowing the method of Kumada (*Tet. Letters*, 52, 5319 (1981)). After cooling to room temperature, the reaction is quenched with water and dilute sodium hydroxide solution and then extracted with ether. The combined organics are dried over MgSO$_4$, filtered and concentrated in vacuo. The residue is purified by flash chromatography on silica gel eluting with ethyl acetate/hexanes (1:3) to provide the desired product.

Examples 102-106 in Table X are prepared under substantially the same conditions as Example 101 from the appropriately substituted quinazolinone starting materials.

TABLE X

[Structure: quinazolinone core substituted with R^5–R^8, linked via CH2 to biphenyl bearing 1H-tetrazole N-protected with C(Ph)$_3$]

| Ex. No. | R^5 | R^6 | R^7 | R^8 | X |
|---|---|---|---|---|---|
| 102 | H | —CH(OTBDMS)CH$_3$ | H | H | —(CH$_2$)$_3$CH$_3$ |
| 103 | H | —CH$_2$OTBDMS | H | H | —(CH$_2$)$_3$CH$_3$ |
| 104 | H | —CH(OTBDMS)CH$_2$CH$_3$ | H | H | —(CH$_2$)$_3$CH$_3$ |
| 105 | H | —C(CH$_3$)$_2$OTBDMS | H | H | —(CH$_2$)$_3$CH$_3$ |
| 106 | H | —CH(OTBDMS)C$_6$H$_5$ | H | H | —(CH$_2$)$_3$CH$_3$ |

*TBDMS = t-butyldimethylsilyl

EXAMPLE 107

2-Butyl-6-(1-hydroxy-1-methylethyl)-3-[[2'-[1-triphenylmethyl)-1H-tetrazol-5-yl][1,1'-biphenyl]-4-yl]methyl]-4(3H)-quinazolinone To a solution of 0.50 g of 2-butyl-6-[1-[[(1,1-dimethylethyl)dimethylsilyl]oxy]-1-methylethyl]-3-[[2'-[1-(triphenylmethyl)-1H-tetrazol-5-yl][1,1'-biphenyl]-4-yl]methyl]-4(3H)-quinazolinone in 15.0 ml of THF is added 0.88 ml of a 1.0M solution of tetrabutylammonium fluoride in THF. The reaction is stirred at room temperature for 1 hour and then poured into 100 ml of water. The aqueous layer is extracted with ether and the combined organics are washed with brine, dried over MgSO$_4$, filtered and concentrated in vacuo. The residue is purified by flash chromatography on silica gel eluting with ethyl acetate/hexanes (1:3) to provide the desired product.

EXAMPLES 108-112 in Table XI are prepared under substantially the same conditions as Example 107 from the appropriately substituted quinazolinone starting materials.

TABLE XI

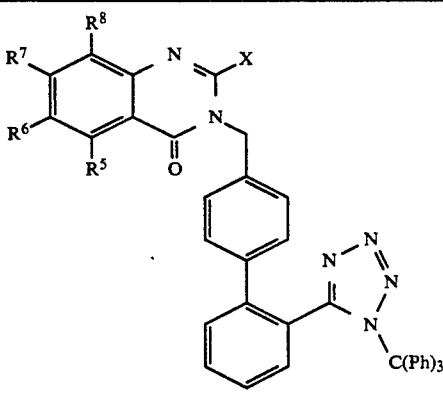

| Ex. No. | R⁵ | R⁶ | R⁷ | R⁸ | X |
|---|---|---|---|---|---|
| 108 | H | —CH(OH)CH₃ | H | H | —(CH₂)₃CH₃ |
| 109 | H | —CH₂OH | H | H | —(CH₂)₃CH₃ |
| 110 | H | —CH(OH)CH₂CH₃ | H | H | —(CH₂)₃CH₃ |
| 111 | H | —C(CH₃)₂OH | H | H | —(CH₂)₃CH₃ |
| 112 | H | —CH(OH)C₆H₅ | H | H | —(CH₂)₃CH₃ |

EXAMPLE 113

5-(2-Bromophenyl)-1-(trimethylstannyl)-1H-tetrazole

To a solution of 1.50 g of o-bromobenzonitrile in 8.0 ml of toluene is added 1.70 g of trimethyltin azide. The reaction mixture is heated to reflux for 18 hours and then allowed to cool to room temperature. The resulting white precipitate is isolated by filtration and used without purification in the next step.

EXAMPLE 114

5-(2-Bromophenyl)-1H-tetrazole

To a solution of 1.0 g of 5-(2-bromophenyl)-1-(trimethylstannyl)-1H-tetrazole in toluene/THF (10:1) at room temperature is added HCl gas, via a bubbler. Gas addition is continued for 5 minutes after the appearance of a precipitate and the solid is then isolated by filtration and washed with hexanes.

EXAMPLE 115

5-(2-Bromophenyl)-1-(triphenylmethyl)-1H-tetrazole

To a solution of 0.50 g of 5-(2-bromophenyl)-1H-tetrazole in 20 ml of CH₂Cl₂ is added 0.65 g of triphenylmethyl chloride followed by 0.37 ml of triethylamine. The solution is refluxed for 2.5 hours, cooled to room temperature and then washed with water, dried over MgSO₄ and concentrated in vacuo. The residue is purified by flash chromatography eluting with ethyl acetate/hexanes (1:5) to provide the desired product.

EXAMPLE 116

2-butyl-6-(1-methoxy-1-methylethyl)-3-[[2'-(1H-tetrazol-5-yl)[1,1'-biphenyl]-4-yl]methyl]-4(3H)-quinazolinone, sodium salt To a solution of 2.488 g of the free tetrazole from Example 57 in 60 ml of methanol is added 5.036 ml of 1.0N sodium hydroxide solution. The mixture is stirred at room temperature for 1 hour and then concentrated in vacuo. The residue is titrated with hexanes, filtered and dried in vacuo to provide 2.29 g of the product as a white solid.

EXAMPLE 117

2-Butyl-6-(1-methoxyethyl)-4-[[2'-(1H-tetrazol)-5-yl)[1,1'-biphenyl]-4-yl]methyl-4(3H)-quinazolinone, sodium salt To a solution of 2.156 g of the free tetrazole from Example 59 in 60 ml of methanol is added 4.359 ml of 1.0N Sodium Hydroxide solution. The mixture is stirred at room temperature for 1 hour and then concentrated in vacuo. The residue is titrated with hexanes, filtered and dried in vacuo to provide 2.09 g of the product as a white solid.

EXAMPLE 118

2-Butyl-6-(methoxymethyl)-4-[[2'-(1H-tetrazol)-5-yl)[1,1'-biphenyl]-4-yl]methyl-4(3H)-quinazolinone To a stirred solution of NaH (500 mg) and primary alcohol from Example 53 in dry THF (35 ml) at 0° C., is added CH₃I (1 ml). The reaction mixture is stirred at room temperature for 4 hours. The reaction mixture is then carefully poured over crushed ice and extracted with chloroform. The organic layer is washed well with water; dried and concentrated. The spongy solid obtained is dissolved in acetone (25 ml) and 5N HCL (3 ml) is added. The reaction mixture is stirred at room temperature for 3 hours. The reaction mixture is then concentrated and the product is purified by column chromatography. Yield: 8.5 mg; m.p: 85° C.

Utility

The performance of the novel compounds of the present invention are shown in the following In Vitro test. The results of this test for representative compounds of the present invention are shown in Table IV.

Angiotensin II Antagonists In Vitro Tests

The source of the angiotensin II receptors utilized in the screen is from rat adrenocortical microsomes. The cortices are placed in ice cold sucrose buffer (0.2 m sucrose, 1 mm EDTA, 10 mm Trizma base, pH 7.4) and homogenized in a chilled ground glass tissue grinder. The homogenate is centrifuged at 3000×g for 10 min. and the resultant supernatant is decanted through cheesecloth and centrifuged at 12,000×g for 3 min. The resulting supernatant is then centrifuged at 1,000,000×g for 60 min. and the pellet resuspended in assay buffer (0.25% bovine serum albumin, 5 mm MgCl₂, 50 mm Trizma base, pH 7.2). Binding assays are performed by incubating aliquots of freshly prepared microsomes in the absence or presence of compound (40 uM final concentration). Ten minutes later, ³H-angiotensin II is added to each tube (2 nM final concentration) and incubated for 60 minutes at 27° C. The reaction is terminated by the addition of 3 ml of cold assay buffer without albumin and the bound and free radioactivity is separated rapidly through glass-fiber filters prewetted with assay buffer. After two additional 3 ml rinses, the filters are placed in scintillation fluid and counted in a scintillation counter to determine trapped radioactivity. Compounds that displace 50% of the labelled angiotensin are considered active compounds and are then evaluated in concentration-response experiments to determine IC₅₀ values. The results ar shown in Table IV.

TABLE IV

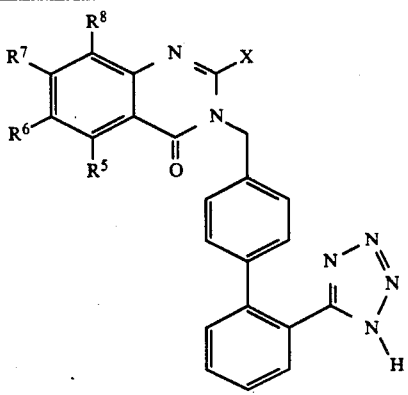

| Ex. No. | R⁵ | R⁶ | R⁷ | R⁸ | X | Angiotensin II Receptor Binding IC$_{50}$(M) |
|---|---|---|---|---|---|---|
| 49 | H | —CH(OH)CH$_3$ | H | H | —(CH$_2$)$_3$CH$_3$ | 8.8 × 10$^{-9}$ |
| 51 | H | —C(CH$_3$)$_2$OH | H | H | —(CH$_2$)$_3$CH$_3$ | 9.4 × 10$^{-9}$ |
| 52 | H | —CH(OH)CH$_2$CH$_3$ | H | H | —(CH$_2$)$_3$CH$_3$ | 1.2 × 10$^{-8}$ |
| 54 | H | (C$_6$H$_5$)CHOH | H | H | —(CH$_2$)$_3$CH$_3$ | >1.0 × 10$^{-5}$ |
| 55 | H | CH$_3$CH$_2$CHOCH$_3$ | H | H | —(CH$_2$)$_3$CH$_3$ | 5.0 × 10$^{-9}$ |
| 56 | H | (C$_6$H$_5$)CHOCH$_3$ | H | H | —(CH$_2$)$_3$CH$_3$ | 8.6 × 10$^{-9}$ |
| 57 | H | (CH$_3$)$_2$COCH$_3$ | H | H | —(CH$_2$)$_3$CH$_3$ | 6.4 × 10$^{-9}$ |
| 58 | H | CH$_3$CHOOCCH$_3$ | H | H | —(CH$_2$)$_3$CH$_3$ | 1.1 × 10$^{-8}$ |
| 60 | H | CH$_3$(CH$_3$O)CH— | H | H | —(CH$_2$)$_3$CH$_3$ | 8.4 × 10$^{-8}$ |
| 64 | H | (CH$_3$)$_2$COCH$_3$ H | H | H | —(CH$_2$)$_3$CH$_3$ | 6.4 × 10$^{-9}$ |
| 66 | H | (C$_6$H$_5$)C(OCH$_3$)— H | H | H | —(CH$_2$)$_3$CH$_3$ | 8.6 × 10$^{-9}$ |
| 68 | H | (C$_2$H$_5$)C(OCH$_3$)— | H | H | —(CH$_2$)$_3$CH$_3$ | 5.0 × 10$^{-9}$ |

The compounds of this invention inhibit the action of AII. By administering a compound of this invention to a rat, and then challenging with angiotensin II, a blackage of the vasopressor response is realized. The results of this test on representative compounds of this invention are shown in Table V.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10–15 minutes with a Gould Brush recorder. (Chan et al., (Drug Development Res., 18:75-94, 1989).

Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 90 and 150 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

The results are shown in Table V and FIG. 1.

TABLE V

| | | | | | | | |
|---|---|---|---|---|---|---|---|
| | | | | | | | |

| | | % INHIBITION (ANGIOTENSIN BLOCKAGE) OF ANGIOTENSIN II (AII) VASOPRESSOR RESPONSE | | | | | |
|---|---|---|---|---|---|---|---|
| Ex. No. | Dose mg/kg iv | AII Dose g/kg iv | Control Before AII | Response After AII | Min. After Dosing Compound | Change | Percent Inhibition (Average) |
|  |  | .05 | 195 | 240 | 0 | 45 |  |
|  |  | .1 | 185 | 240 |  | 55 |  |
| 49 | 1 | .05 | 190 | 217 | 30 | 27 | 40 |
|  |  | .1 | 185 | 225 |  | 40 | 27 |
| 49 | 1 | .05 | 170 | 195 | 45 | 25 | 45 |
|  |  | .1 | 185 | 210 |  | 25 | 55 |
|  |  | .05 | 170 | 210 | 90 | 40 | 11 |
|  |  | .1 | 185 | 225 |  | 40 | 27 |
| 49 | 2 | .05 | 190 | 200 | 120 | 10 | 78 |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
|  |  | .1 | 185 | 220 |  | 35 | 36 |
|  |  | .05 | 190 | 225 | 150 | 35 | 23 |
|  |  | .1 | 190 | 230 |  | 40 | 27 |
|  |  | .05 | 175 | 225 | 180 | 50 | 11 |
|  |  | .1 | 175 | 230 |  | 55 | 0 |
|  |  | .05 | 220 | 254 | 0 | 26 |  |
|  |  | .05 | 205 | 235 | 0 | 30 |  |
|  |  | 0.1 | 223 | 272 | 0 | 44 |  |
|  |  | 0.1 | 205 | 250 | 0 | 45 |  |
| 49 |  | .05 | 253 | 253 | 30 | 0 |  |
|  | 10 | .05 | 190 | 190 | 30 | 0 | 100 |
|  |  | 0.1 | 243 | 243 | 30 | 0 |  |
|  |  | 0.1 | 190 | 190 | 30 | 0 | 100 |
|  |  | .05 | 228 | 228 | 90 | 0 |  |
|  |  | .05 | 185 | 185 | 90 | 0 | 100 |
|  |  | .05 | 185 | 230 | 0 | 45 |  |
|  |  |  | 185 | 225 |  | 40 |  |
|  |  | 1. | 180 | 235 |  | 55 |  |
|  |  |  | 185 | 235 |  | 50 |  |
| 50 | 30 | .05 | 175 | 190 | 30 | 15 | 82 |
|  |  |  | 190 | 190 |  | 0 |  |
|  |  | 1. | 170 | 195 |  | 25 | 76 |
|  |  |  | 190 | 190 |  | 0 |  |
|  |  | .05 | 170 | 200 | 90 | 30 | 29 |
|  |  |  | 180 | 215 |  | 30 |  |
|  |  | 1. | 180 | 210 |  | 30 | 52 |
|  |  |  | 185 | 205 |  | 20 |  |
|  |  | .05 | 170 | 200 | 150 | 30 | 41 |
|  |  |  | 170 | 190 |  | 20 |  |
|  |  | 1. | 185 | 220 |  | 35 | 48 |
|  |  |  | 170 | 190 |  | 20 |  |
|  |  | .05 | 220 | 260 | 0 | 40 |  |
|  |  | .05 | 200 | 232 | 0 | 32 |  |
|  |  | 0.1 | 215 | 265 | 0 | 50 |  |
|  |  | 0.1 | 200 | 240 | 0 | 40 |  |
| 51 | 5* | .05 | 205 | 235 | 30 | 30 |  |
|  |  | .05 | 185 | 210 | 30 | 25 | 30 |
|  |  | 0.1 | 200 | 240 | 30 | 40 |  |
|  |  | 0.1 | 190 | 215 | 30 | 25 | 26 |
|  |  | .05 | 205 | 210 | 90 | 5 |  |
|  |  | .05 | 180 | 193 | 90 | 13 | 75 |
|  |  | 0.1 | 200 | 225 | 90 | 25 |  |
|  |  | 0.1 | 180 | 195 | 90 | 15 | 55 |
|  |  | .05 | 190 | 205 | 150 | 15 |  |
|  |  | .05 | 180 | 190 | 150 | 10 | 63 |
|  |  | 0.1 | 190 | 217 | 150 | 27 |  |
|  |  | 0.1 | 180 | 200 | 150 | 20 | 46 |
|  |  | .05 | 235 | 285 | 0 | 50 |  |
|  |  | .1 | 225 | 285 |  | 60 |  |
| *51 | 1 | .05 | 220 | 260 | 30 | 40 | 20 |
|  |  | .1 | 220 | 275 |  | 55 | 8 |
| *51 | 1 | .05 | 220 | 245 | 45 | 25 | 50 |
|  |  | .1 | 220 | 260 |  | 40 | 33 |
|  |  | .05 | 220 | 265 | 90 | 45 | 10 |
|  |  | .1 | 210 | 275 |  | 65 | 8 |
| *51 *sodium salt | 2 | .05 | 225 | 250 | 120 | 25 | 50 |
|  |  | .1 | 215 | 265 |  | 50 | 17 |
|  |  | .05 | 225 | 260 | 150 | 35 | 30 |
|  |  | .1 | 225 | 270 |  | 45 | 25 |
|  |  | .05 | 225 | 265 | 180 | 40 | 20 |
|  |  | .1 | 235 | 280 |  | 45 | 25 |
|  |  | .05 | 210 | 265 | 0 | 55 |  |
|  |  | .05 | 205 | 255 | 0 | 50 |  |
|  |  | 0.1 | 215 | 275 | 0 | 60 |  |
|  |  | 0.1 | 210 | 265 | 0 | 55 |  |
| 52 | 5 oral | .05 | 205 | 230 | 30 | 25 |  |
|  |  | .05 | 190 | 215 | 30 | 25 | 52 |
|  |  | 0.1 | 205 | 240 | 30 | 35 |  |
|  |  | 0.1 | 190 | 220 | 30 | 30 | 43 |
|  |  | .05 | 185 | 205 | 90 | 20 |  |
|  |  | .05 | 185 | 200 | 90 | 15 | 66 |
|  |  | 0.1 | 185 | 205 | 90 | 20 |  |
|  |  | 0.1 | 185 | 206 | 90 | 21 | 63 |
|  |  | .05 | 180 | 195 | 150 | 15 |  |
|  |  | .05 | 175 | 180 | 150 | 15 | 71 |
|  |  | 0.1 | 175 | 201 | 150 | 26 |  |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
| | | 0.1 | 180 | 200 | 150 | 20 | 60 |
| | | .05 | 165 | 220 | 0 | 55 | |
| | | | 185 | 230 | | 45 | |
| | | .1 | 175 | 220 | | 45 | |
| | | | 190 | 240 | | 50 | |
| 53 | 10 | .05 | 155 | 157 | 10 | 2 | 83 |
| | | | 140 | 155 | | 15 | |
| | | .1 | 155 | 165 | | 10 | 90 |
| | | | 130 | 130 | | 0 | |
| | | .05 | 155 | 160 | 30 | 5 | 85 |
| | | | 135 | 145 | | 10 | |
| | | .1 | 160 | 165 | | 5 | 84 |
| | | | 155 | 165 | | 10 | |
| | | .05 | 160 | 175 | 60 | 15 | 65 |
| | | | 140 | 160 | | 20 | |
| | | .1 | 165 | 180 | | 15 | 68 |
| | | | 150 | 165 | | 15 | |
| | | .05 | 200 | 245 | 0 | 45 | |
| | | | 175 | 222 | | 47 | |
| | | | 185 | 230 | | 45 | |
| | | .1 | 200 | 252 | | 47 | |
| | | | 170 | 217 | | 55 | |
| | | | 180 | 235 | | 55 | |
| 53 | 10 | | | | 30 | | |
| | | .05 | 210 | 245 | | 35 | 17 |
| | | | 175 | 215 | | 40 | |
| | | | 185 | 225 | | 40 | |
| | | .1 | 205 | 250 | | 45 | 19 |
| | | | 175 | 220 | | 45 | |
| | | | 195 | 232 | | 37 | |
| | | | | | 60 | | |
| 53 | | .05 | 192 | 237 | | 45 | 27 |
| | | | 170 | 190 | | 20 | |
| | | | 175 | 210 | | 35 | |
| | | .1 | 195 | 245 | | 50 | 4 |
| | | | 170 | 220 | | 50 | |
| | | | 175 | 225 | | 50 | |
| | | | | | 90 | | |
| | | .05 | 205 | 245 | | 40 | 41 |
| | | | 175 | 195 | | 20 | |
| | | | 185 | 207 | | 22 | |
| | | .1 | 200 | 250 | | 50 | 56 |
| | | | 175 | 210 | | 35 | |
| | | | 177 | 225 | | 48 | |
| | | | | | 30 | | |
| | | .05 | 207 | 225 | | 18 | 76 |
| | | | 167 | 190 | | 23 | |
| | | | 180 | 210 | | 30 | |
| | | .1 | 200 | 255 | | 55 | 60 |
| | | | 175 | 197 | | 22 | |
| | | | 180 | 223 | | 43 | |
| | | | | | 60 | | |
| | | .05 | 200 | 240 | | 40 | 46 |
| | | | 170 | 180 | | 10 | |
| | | | 200 | 225 | | 25 | |
| 53 | | .1 | 207 | 250 | | 43 | 44 |
| | | | 170 | 190 | | 20 | |
| | | | 190 | 230 | | 40 | |
| | | | | | 90 | | |
| | | .05 | 195 | 235 | | 40 | 35 |
| | | | 165 | 180 | | 15 | |
| | | | 180 | 215 | | 35 | |
| | | .1 | 200 | 250 | | 50 | 26 |
| | | | 175 | 190 | | 15 | |
| | | | 180 | 230 | | 50 | |
| | | .05 | 210 | 275 | 0 | 65 | |
| | | | 230 | 270 | | 40 | |
| | | .1 | 210 | 280 | | 70 | |
| | | | 235 | 280 | | 45 | |
| 53 | 6 | .05 | 200 | 220 | 30 | 20 | 67 |
| | | | 210 | 225 | | 15 | |
| | | .1 | 205 | 220 | | 15 | 70 |
| | | | 210 | 230 | | 20 | |
| | | .05 | 205 | 225 | 90 | 20 | 48 |
| | | | 200 | 235 | | 35 | |
| | | .1 | 205 | 240 | | 35 | 30 |
| | | | 205 | 250 | | 45 | |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
| 53 | 6 | .025 | 235 | 265 | 0 | 30 | |
| | | .05 | 235 | 265 | | 30 | |
| | | .1 | 235 | 265 | | 30 | |
| 53 | 6 | .025 | 210 | 225 | 30 | 15 | 50 |
| | | .05 | 210 | 235 | | 25 | 17 |
| | | .1 | 215 | 250 | | 35 | 17 |
| | | .025 | 200 | 210 | 90 | 10 | |
| | | .05 | 190 | 225 | | 35 | 17 |
| | | .1 | 200 | 235 | | 35 | 17 |
| | | .05 | 187 | 240 | 0 | 53 | |
| | | | 213 | 260 | | 47 | |
| | | .1 | 187 | 240 | | 53 | |
| | | | 215 | 265 | | 50 | |
| 53 | 3 | .05 | 175 | 205 | 10 | 30 | 62 |
| | | | 207 | 215 | | 8 | |
| | | .1 | 175 | 215 | | 40 | 42 |
| | | | 205 | 225 | | 20 | |
| | | .05 | 175 | 210 | 30 | 35 | 45 |
| | | | 210 | 2340 | | 20 | |
| | | .1 | 190 | 220 | | 30 | 47 |
| | | | 215 | 235 | | 20 | |
| | | .05 | 175 | 215 | 60 | 40 | 30 |
| | | | 210 | 240 | | 30 | |
| | | .1 | 180 | 235 | | 55 | 13 |
| | | | 220 | 255 | | 35 | |
| | | .05 | 210 | 270 | 0 | 60 | |
| | | | 225 | 265 | | 40 | |
| | | .1 | 205 | 275 | | 70 | |
| | | | 235 | 290 | | 55 | |
| 53 | 3 | .05 | 200 | 215 | 30 | 15 | 55 |
| | | | 230 | 260 | | 30 | |
| | | .1 | 195 | 215 | | 20 | 44 |
| | | | 220 | 270 | | 50 | |
| | | .05 | 200 | 225 | 90 | 25 | 25 |
| | | | 225 | 275 | | 50 | |
| | | .1 | 200 | 235 | | 35 | 13 |
| | | | 225 | 277 | | 52 | |
| 53 | 3 | .05 | 175 | 190 | 30 | 15 | 60 |
| | | | 225 | 250 | | 25 | |
| | | .1 | 180 | 210 | | 30 | 36 |
| | | | 225 | 250 | | 50 | |
| | | .05 | 200 | 250 | 0 | 50 | |
| | | | 210 | 265 | | 55 | |
| | | .1 | 200 | 255 | | 55 | |
| | | | 200 | 265 | | 65 | |
| 53 | 3 | .05 | 185 | 210 | 30 | 25 | 67 |
| | | | 190 | 200 | | 10 | |
| | | .1 | 185 | 205 | | 20 | 67 |
| | | | 190 | 210 | | 20 | |
| | | .05 | 185 | 235 | 90 | 50 | 10 |
| | | | 195 | 260 | | 65 | |
| | | .1 | 190 | 235 | | 45 | 17 |
| | | | 200 | 255 | | 55 | |
| | | .025 | 220 | 260 | | 40 | |
| | | | 210 | 255 | | 45 | |
| | | .05 | 220 | 265 | | 45 | |
| | | | 210 | 260 | | 50 | |
| | | .1 | 220 | 275 | | 55 | |
| | | | 215 | 265 | | 50 | |
| 53 | 3 | .025 | 210 | 225 | 30 | 15 | 53 |
| | | | 195 | 220 | | 25 | |
| 53 | | .05 | 207 | 220 | | 13 | 65 |
| | | | 190 | 210 | | 20 | |
| | | .1 | 210 | 235 | | 25 | 52 |
| | | | 190 | 215 | | 25 | |
| | | .025 | 210 | 230 | 90 | 20 | 47 |
| | | | 185 | 210 | | 25 | |
| | | .05 | 210 | 240 | | 30 | 35 |
| | | | 190 | 222 | | 32 | |
| | | .1 | 210 | 250 | | 40 | |
| | | | 195 | 235 | | 40 | 24 |
| | | .05 | 190 | 235 | 0 | 45 | |
| | | | 210 | 255 | | 65 | |
| | | .1 | 190 | 245 | | 55 | |
| | | | 210 | 255 | | 45 | |
| 54 | 1 | .05 | 190 | 215 | 30 | 25 | 47 |
| | | | 205 | 227 | | 32 | |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
| | | .1 | 195 | 230 | | 35 | 30 |
| | | | 210 | 245 | | 35 | |
| 54 | 1 | .05 | 190 | 207 | 45 | 17 | 75 |
| | | | 205 | 215 | | 10 | |
| | | .1 | 185 | 230 | | 45 | 28 |
| | | | 200 | 227 | | 27 | |
| | | .05 | 190 | 217 | 90 | 27 | 49 |
| | | | 210 | 240 | | 30 | |
| | | .1 | 200 | 240 | | 40 | 34 |
| | | | 210 | 235 | | 25 | |
| 54 | 2 | .05 | 220 | 220 | 120 | 0 | 85 |
| | | | 200 | 215 | | 15 | |
| | | .1 | 202 | 222 | | 20 | 64 |
| | | | 200 | 215 | | 15 | |
| | | .05 | 185 | 205 | 150 | 20 | 67 |
| | | | 195 | 210 | | 15 | |
| | | .1 | 190 | 215 | | 25 | 54 |
| | | | 195 | 215 | | 20 | |
| | | .05 | 190 | 207 | 180 | 17 | 69 |
| | | | 190 | 207 | | 17 | |
| | | .1 | 190 | 220 | | 30 | 50 |
| | | | 190 | 210 | | 20 | |
| 54 | 5 P.O.* | | | | | | |
| | | 0.05 | 210 | 235 | 180 | 25 | 55 |
| | | 0.1 | 197 | 245 | | 48 | 26 |
| *oral dosage | | | | | | | |
| | | .05 | 200 | 255 | 0 | 55 | |
| | | .1 | 200 | 255 | | 55 | |
| 55 | 30 | .05 | 180 | 190 | 30 | 10 | 82 |
| | | .1 | 180 | 195 | | 15 | 73 |
| | | .05 | 170 | 185 | 90 | 15 | 73 |
| | | .1 | 170 | 175 | | 5 | 91 |
| | | .05 | 185 | 205 | 150 | 20 | 64 |
| | | .1 | 190 | 195 | | 5 | 91 |
| | | .025 | 230 | 260 | 0 | 30 | |
| | | .05 | 225 | 270 | | 45 | |
| | | .1 | 235 | 283 | | 48 | |
| 57 | 1 | .025 | 205 | 220 | 15 | 15 | 50 |
| | | .05 | 220 | 225 | | 5 | 89 |
| | | .1 | 217 | 242 | | 25 | 48 |
| | | .025 | 215 | 230 | 30 | 15 | 50 |
| | | .05 | 225 | 235 | | 10 | 78 |
| | | .1 | 225 | 260 | | 35 | 27 |
| | | .025 | 240 | 245 | 60 | 5 | 83 |
| | | .05 | 240 | 255 | | 15 | 67 |
| | | .1 | 240 | 275 | | 35 | 27 |
| 57 | 2 | .025 | 230 | 255 | 90 | 25 | 17 |
| | | .05 | 225 | 235 | | 10 | 78 |
| | | .1 | 225 | 255 | | 30 | 37 |
| | | .025 | 205 | 265 | 120 | 60 | 100 |
| | | .05 | 225 | 255 | | 30 | 33 |
| | | .1 | 235 | 255 | | 20 | 58 |
| 57 | 3 | .025 | 210 | 225 | 150 | 15 | 50 |
| | | .05 | 215 | 230 | | 15 | 67 |
| | | .1 | 215 | 240 | | 25 | 48 |
| | | .025 | 207 | 250 | 0 | 43 | |
| | | | 210 | 260 | | 50 | |
| | | .05 | 215 | 253 | | 38 | |
| | | | 210 | 265 | | 55 | |
| | | .1 | 220 | 265 | | 45 | |
| | | | 220 | 265 | | 45 | |
| 57 | *5 | .025 | 205 | 210 | 30 | 5 | 94 |
| | | | 205 | 205 | | 0 | |
| | | .05 | 200 | 207 | | 7 | 77 |
| | | | 200 | 215 | | 15 | |
| | | .1 | 198 | 215 | | 17 | 64 |
| | | | 200 | 215 | | 15 | |
| | | .025 | 205 | 215 | 60 | 10 | 89 |
| | | | 195 | 195 | | 0 | |
| | | .05 | 215 | 215 | | 0 | 87 |
| | | | 193 | 205 | | 12 | |
| | | .1 | 200 | 217 | | 17 | 58 |
| | | | 190 | 210 | | 20 | |
| | | .025 | 195 | 200 | 120 | 5 | 94 |
| | | | 200 | 200 | | 0 | |
| | | .05 | 195 | 210 | | 15 | 72 |
| | | | 200 | 210 | | 10 | |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
| | | .1 | 192 | 220 | | 28 | 40 |
| | | | 200 | 225 | | 25 | |
| | | .025 | 195 | 210 | 180 | 15 | 72 |
| | | | 200 | 210 | | 10 | |
| | | .05 | 200 | 215 | | 15 | 68 |
| | | | 200 | 215 | | 15 | |
| *oral dosage | | | | | | | |
| | | .1 | 200 | 215 | | 15 | 56 |
| | | | 200 | 225 | | 25 | |
| | | .025 | 220 | 220 | 240 | 0 | 100 |
| | | | 190 | 190 | | 0 | |
| | | ..05 | 195 | 210 | | 15 | 62 |
| | | | 180 | 200 | | 20 | |
| | | .1 | 220 | 235 | | 15 | 49 |
| | | | 185 | 215 | | 30 | |
| | | .05 | 200 | 260 | 0 | 60 | |
| | | | 210 | 257 | | 47 | |
| | | .1 | 205 | 260 | | 55 | |
| | | | 200 | 260 | | 60 | |
| 58 | 30 | .05 | 195 | 205 | 30 | 10 | 87 |
| | | | 222 | 225 | | 3 | |
| | | .1 | 205 | 205 | | 0 | 98 |
| | | | 205 | 206 | | 2 | |
| | | .05 | 190 | 190 | 90 | 0 | 85 |
| | | | 210 | 225 | | 15 | |
| | | .1 | 195 | 195 | | 0 | 95 |
| | | | 210 | 215 | | 5 | |
| | | .05 | 180 | 190 | 150 | 10 | 85 |
| | | | 200 | 205 | | 5 | |
| | | .1 | 190 | 207 | | 17 | 81 |
| | | | 205 | 210 | | 5 | |
| | | .05 | 235 | 285 | 0 | 50 | |
| | | | 230 | 290 | | 60 | |
| | | .1 | 225 | 285 | | 60 | |
| | | | 230 | 285 | | 55 | |
| 60 | 1 | .05 | 207 | 232 | 30 | 25 | 55 |
| | | | 215 | 240 | | 25 | |
| | | .1 | 215 | 260 | | 45 | 17 |
| | | | 210 | 260 | | 50 | |
| 60 | 1 | .05 | 195 | 205 | 45 | 10 | 82 |
| | | | 215 | 225 | | 10 | |
| | | .1 | 190 | 215 | | 25 | 43 |
| | | | 210 | 250 | | 40 | |
| | | .05 | 210 | 230 | 90 | 20 | 58 |
| | | | 210 | 235 | | 25 | |
| | | .1 | 215 | 245 | | 30 | 43 |
| | | | 210 | 245 | | 35 | |
| 60 | 2 | .05 | 215 | 215 | 120 | 0 | 100 |
| | | | 220 | 220 | | 0 | |
| | | .1 | 210 | 220 | | 10 | 86 |
| | | | 220 | 225 | | 5 | |
| | | .05 | 220 | 225 | 150 | 5 | 82 |
| | | | 205 | 220 | | 15 | |
| | | .1 | 215 | 225 | | 10 | 52 |
| | | | 205 | 250 | | 45 | |
| | | .05 | 215 | 240 | 180 | 25 | 45 |
| | | | 210 | 245 | | 35 | |
| 60 | | .1 | 215 | 250 | | 35 | 31 |
| | | | 205 | 250 | | 45 | |
| | | .025 | 195 | 209 | 0 | 14 | |
| | | .025 | 200 | 218 | 0 | 18 | |
| | | .05 | 200 | 215 | 0 | 15 | |
| | | .05 | 195 | 228 | 0 | 33 | |
| | | 0.1 | 200 | 220 | 0 | 20 | |
| | | 0.1 | 200 | 250 | 0 | 50 | |
| 61 | 2 | .025 | 195 | 195 | 30 | 0 | |
| | | .025 | 200 | 200 | 30 | 0 | 100 |
| | | .05 | 190 | 190 | 30 | 0 | |
| | | .05 | 180 | 180 | 30 | 0 | 100 |
| | | 0.1 | 165 | 165 | 30 | 0 | |
| | | 0.1 | 220 | 220 | 30 | 0 | 100 |
| | | .025 | 190 | 190 | 90 | 0 | |
| | | .025 | 197 | 197 | 90 | 0 | 100 |
| | | .05 | 185 | 185 | 90 | 0 | |
| | | .05 | 200 | 200 | 90 | 0 | 100 |
| | | 0.1 | 185 | 185 | 90 | 0 | |
| | | 0.1 | 205 | 205 | 90 | 0 | 100 |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
| | | .025 | 180 | 180 | 140 | 0 | |
| | | .025 | 200 | 200 | 150 | 0 | 100 |
| | | .05 | 180 | 180 | 150 | 0 | |
| | | .05 | 195 | 195 | 150 | 0 | 100 |
| | | 0.1 | 185 | 185 | 150 | 0 | |
| | | 0.1 | 180 | 194 | 150 | 14 | 80 |
| | | | 180 | 200 | | 20 | |
| | | .025 | 200 | 210 | 0 | 10 | |
| | | .025 | 215 | 225 | 0 | 10 | |
| | | .05 | 200 | 220 | 0 | 20 | |
| | | .05 | 215 | 235 | 0 | 20 | |
| | | 0.1 | 210 | 235 | 0 | 25 | |
| | | 0.1 | 215 | 245 | 0 | 30 | |
| 64 | 2 | .025 | 195 | 195 | 30 | 0 | |
| | | .025 | 190 | 190 | 30 | 0 | 100 |
| | | .05 | 195 | 195 | 30 | 0 | |
| | | .05 | 190 | 190 | 30 | 0 | 100 |
| | | 0.1 | 195 | 195 | 30 | 0 | |
| | | 0.1 | 195 | 195 | 30 | 0 | 100 |
| | | .025 | 185 | 185 | 90 | 0 | |
| | | .025 | 185 | 185 | 90 | 0 | 100 |
| | | .05 | 190 | 190 | 90 | 0 | |
| | | .05 | 185 | 185 | 90 | 0 | 100 |
| | | 0.1 | 190 | 190 | 90 | 0 | |
| | | 0.1 | 190 | 190 | 90 | 0 | 100 |
| | | .025 | 190 | 190 | 150 | 0 | |
| | | .025 | 185 | 185 | 150 | 0 | 100 |
| | | .05 | 185 | 185 | 150 | 0 | |
| | | .05 | 185 | 185 | 150 | 0 | 100 |
| | | 0.1 | 185 | 185 | 150 | 0 | |
| | | 0.1 | 185 | 195 | 150 | 10 | 82 |
| | | | 185 | 215 | | 30 | |
| | | | 180 | 213 | | 33 | |
| | | .05 | 220 | 255 | 0 | 35 | |
| | | | 210 | 250 | | 40 | |
| | | .1 | 215 | 255 | | 40 | |
| | | | 210 | 257 | | 47 | |
| 64 | 5 P.O.* | .05 | 195 | 217 | 30 | 22 | 45 |
| | | | 200 | 220 | | 20 | |
| | | .1 | 200 | 225 | | 25 | 32 |
| | | | 200 | 235 | | 35 | |
| | | .05 | 197 | 215 | 60 | 18 | 50 |
| | | | 190 | 210 | | 20 | |
| | | .1 | 195 | 225 | | 30 | 25 |
| | | | 195 | 230 | | 35 | |
| | | .05 | 190 | 200 | 90 | 10 | 61 |
| | | | 185 | 205 | | 20 | |
| | | .1 | 185 | 210 | | 25 | 36 |
| | | | 190 | 220 | | 30 | |
| | | .05 | 185 | 205 | 120 | 20 | 47 |
| | | | 200 | 220 | | 20 | |
| | | .1 | 185 | 210 | | 25 | 41 |
| | | | 200 | 227 | | 27 | |
| | | .05 | 185 | 195 | 180 | 10 | 49 |
| | | | 195 | 220 | | 25 | |
| | | .1 | 190 | 207 | | 17 | 41 |
| | | | 195 | 230 | | 35 | |
| oral dosage | | | | | | | |
| 64 | | .05 | 190 | 200 | 240 | 10 | 49 |
| | | | 195 | 220 | | 25 | |
| | | .1 | 190 | 205 | | 15 | 48 |
| | | | 195 | 225 | | 30 | |
| | | .025 | 215 | 245 | 0 | 30 | |
| | | .05 | 220 | 255 | | 35 | |
| | | .1 | 220 | 255 | | 35 | |
| 66 | 1 | .025 | 207 | 225 | 15 | 18 | 40 |
| | | .05 | 210 | 225 | | 15 | 57 |
| | | .1 | 215 | 230 | | 15 | 57 |
| | | .025 | 205 | 227 | 30 | 27 | 27 |
| | | .05 | 215 | 230 | | 15 | 57 |
| | | .1 | 215 | 235 | | 20 | 43 |
| | | .025 | 210 | 230 | 60 | 20 | 33 |
| | | .05 | 210 | 230 | | 20 | 43 |
| | | .1 | 210 | 240 | | 30 | 14 |
| 66 | 2 | .025 | 195 | 205 | 90 | 10 | 67 |
| | | .05 | 205 | 220 | | 15 | 57 |
| | | .1 | 205 | 210 | | 5 | 86 |

TABLE V-continued

% INHIBITION (ANGIOTENSIN BLOCKAGE) OF ANGIOTENSIN II (AII) VASOPRESSOR RESPONSE

| Ex. No. | Dose mg/kg iv | AII Dose g/kg iv | Control Before AII | Response After AII | Min. After Dosing Compound | Change | Percent Inhibition (Average) |
|---|---|---|---|---|---|---|---|
|  |  | .025 | 200 | 220 | 120 | 20 | 33 |
|  |  | .05 | 200 | 215 |  | 15 | 57 |
|  |  | .1 | 190 | 205 |  | 15 | 57 |
|  |  | .025 | 180 | 195 | 150 | 15 | 50 |
|  |  | .05 | 190 | 200 |  | 10 | 71 |
|  |  | .1 | 185 | 205 |  | 20 | 43 |
|  |  | .05 | 200 | 255 | 0 | 55 |  |
|  |  | .1 | 200 | 255 |  | 55 |  |
| 68 | 30 | .05 | 180 | 190 | 30 | 10 | 82 |
|  |  | .1 | 180 | 195 |  | 15 | 73 |
|  |  | .05 | 170 | 185 | 90 | 15 | 73 |
|  |  | .1 | 170 | 175 |  | 5 | 91 |
|  |  | .05 | 185 | 205 | 150 | 20 | 64 |
|  |  | .1 | 190 | 195 |  | 5 | 91 |

Antihypertensive Effects in Conscious Aorta-Coarcted Renin/Angiotensin II-Dependent Renal Hypertensive Rats Following the method reported by Chan et al., Drug Development Res. 18: 75–94, 1989, hypertension is induced by complete ligation of the aorta between the origin of the renal arteries according to the method of Rojo-Ortega and Genest (Can. J. Physio Pharmacol 46: 883–885, 1968.) and Fernandes et al., (J. Lab. Clin. Med. 87: 561–567, 1976) with modifications of the surgery procedures. Male Sprague-Dawley rats (Charles River Labs., Inc., Wilmington, Mass.) of 350 to 400 gm body weight are anesthetized with methohexital sodium (Brevital sodium, Eli Lilly and Co.) 60 mg/kg i.p. An incision is made in the left flank parallel to the rib cage. Using No. 3-0 silk suture(Davis & Geck, Pearl River, NY), the aorta is completely ligated between the origins of the renal arteries. The wound is closed, and the animals returned to their individual cages. On the 7th day after aortic coarctation, the rats are used. The rats are restrained in a supine position with elastic tape, and the heads are immobilized by gentle restraining. The ventral portion of the neck is locally anesthetized by subcutaneous infiltration with 2% lidocaine. The left carotid artery is isolated and cannulated with a length of PE50 tubing, which is in turn, connected to a Statham P23Db pressure transducer - Beckman Dynagraph recording system. In some studies, the cannular is exteriorized through the back of the neck for long period of blood pressure monitoring. Recordings are taken over a 15–20 minute period, and the rats are dosed with the test compounds or vehicle (saline). After dosing, the blood pressure is monitored continuously. The results are shown in FIGS. 2 to 7.

When the compounds are employed for the above utility, they may be combined with one or more pharmaceutically acceptable carriers, for example. solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. for example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. The compound 2-butyl-6-(1-methoxy-1-methylethyl)-3-[[2'-(1H-tetrazol-5-yl)[1,1'-biphenyl]-4-yl]methyl]-4(3H)-quinazolinone, sodium salt.

2. The compound 2-butyl-6-(1-methoxy-1-methylethyl)-3-[[2'-(1H-tetrazol-5-yl)[1,1'-biphenyl]-4-yl]methyl]-4(3H)-quinazolinone.

3. A pharmaceutical composition useful for treating angiotensin induced hypertension or congestive heart failure in a mammal comprising a suitable pharmaceutical carrier and an effective amount of a compound of claim 1.

4. A method of treating angiotensin induced hypertension in a mammal comprising administering a compound of claim 1 to said mammal an amount effective to lower angiotensin induced hypertension.

5. A method of treating congestive heart failure in a mammal comprising administering a compound of claim 1 to said mammal in an amount effective to treat congestive heart failure.

* * * * *